US008518654B2

(12) United States Patent
Ueda et al.

(10) Patent No.: US 8,518,654 B2
(45) Date of Patent: Aug. 27, 2013

(54) LUNG CANCER DIAGNOSTIC POLYPEPTIDE, METHOD FOR DETECTING LUNG CANCER, AND METHOD FOR EVALUATING THERAPEUTIC EFFECT

(75) Inventors: Koji Ueda, Kanagawa (JP); Hidewaki Nakagawa, Kanagawa (JP); Atsuhiko Toyama, Tokyo (JP); Taka-Aki Sato, Tokyo (JP)

(73) Assignees: Riken, Wako-Shi, Saitama (JP); Shimadzu, Nakagyo-Ku (JP)

( * ) Notice: Subject to any disclaimer, the term of this patent is extended or adjusted under 35 U.S.C. 154(b) by 0 days.

(21) Appl. No.: 13/197,849

(22) Filed: Aug. 4, 2011

(65) Prior Publication Data

US 2012/0040376 A1 Feb. 16, 2012

(51) Int. Cl.
*G01N 33/53* (2006.01)
*C12N 5/00* (2006.01)

(52) U.S. Cl.
USPC .............................. 435/7.1; 435/7.23; 436/64

(58) Field of Classification Search
None
See application file for complete search history.

(56) References Cited

PUBLICATIONS

Ueda et al , PLoS ONE 6: e18567, published Apr. 2011, p. 1-12.*
M.H. Gail et al., "Multiple Markers for Lung Cancer Diagnosis: Validation of Models for Localized Lung Cancer" *J. National Cancer Inst*, vol. 80, No. 2, pp. 97-101 (1988).
N.J. McCarthy et al., "Tumor Markers: Should we or Shouldn't We?" *The Cancer Journal*, vol. 7, No. 3, pp. 175-177 (2001).
M.D. Brundage et al., "Prognostic Factors in Non-small Cell Lung Cancer: A Decade of Progress" *Chest*, 122, pp. 1037-1057 (2002).
H-J. Sung et al., "Biomarkers for the lung cancer diagnosis and their advances in proteomics" *BMB Reports*, 41(9), pp. 615-625, (2008).
P. Maurya et al., "Proteomic Approaches for Serum Biomarker Discovery in Cancer" *Anticancer Research*, 27, pp. 1247-1255 (2007).
A. Gamez-Pozo et al., "MALDI Profiling of Human Lung Cancer Subtypes" *PLOS One*, vol. 4, Issue 11, E7731, pp. 1-6 (2009).
B. Wollscheid et al., "Mass-spectrometric identification and relative quantification of N-linked cell surface glycoproteins" *Nature Biotechnology*, vol. 27, No. 4, pp. 378-386 (2009) with Corrigenda & Errata, *Nat. Biotechnology.* vol. 27, No. 9, p. 864 (2009).
R. Scheiss et al., "Targeted proteomic strategy for clinical biomarker discovery" *Molecular Oncology* 3, pp. 33-44 (2009).
K. Ueda et al, "Development of Serum Glycoproteomic Profiling Technique; Simultaneous Identification of Glycosylation Sites and Site-Specific Quantification of Glycan Structure Changes" *Molecular & Cellular Proteomics*, 9.9, pp. 1819-1828 (2010).
J. Villanueva et al., "Monitoring peptidase activities in complex proteomes by MALDI-TOF mass spectrometry" *Nature Protocols*, vol. 4, No. 8, pp. 1167-1183 (2009).
K. Ueda et al., "Application of quantitative peptidomics for the identification of serum lung cancer biomarkers" *AACR-JCA 8th Joint Conference; Cancer Genomics, Epigenomics, and the Development of Novel Therapeutics*, (2010).
C. Lopez-Otin et al., "Proteases: Multifunctional Enzymes in Life and Disease" *Journal of Biological Chemistry*, vol. 283, No. 45, pp. 30433-30437 (2008).
C.M. Overall, et al, "In search of partners: inking extracellular proteases to substrates" *Nature Reviews, Molecular Cell Biology*, vol. 8, pp. 245-257 (2007).
C. Palermo et al., "Cysteine cathespin proteases as pharmacological targets in cancer" *TRENDS in Pharmacological Sciences*, vol. 29, No. 1, pp. 22-28 (2008).
C. Lopez-Otin et al., "Emerging Roles of proteases in tumour suppression" *Nature Reviews Cancer*, vol. 7, pp. 800-808 (2007).
M. Egeblad et al., "New Functions for the Matrix Metalloproteinases in Cancer Progression" *Nature Reviews, Cancer*, vol. 2, pp. 161-174 (2002).

\* cited by examiner

*Primary Examiner* — Lei Yao
(74) *Attorney, Agent, or Firm* — Edwards Wildman Palmer LLP; David G. Conlin; Lisa Swiszcz

(57) ABSTRACT

A novel biomarker for use in lung cancer diagnosis is provided.

21 Claims, 18 Drawing Sheets

FIG. 6 (cont.)
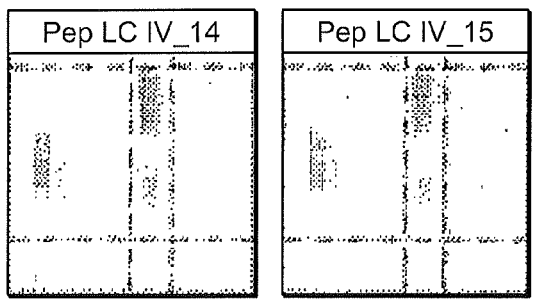
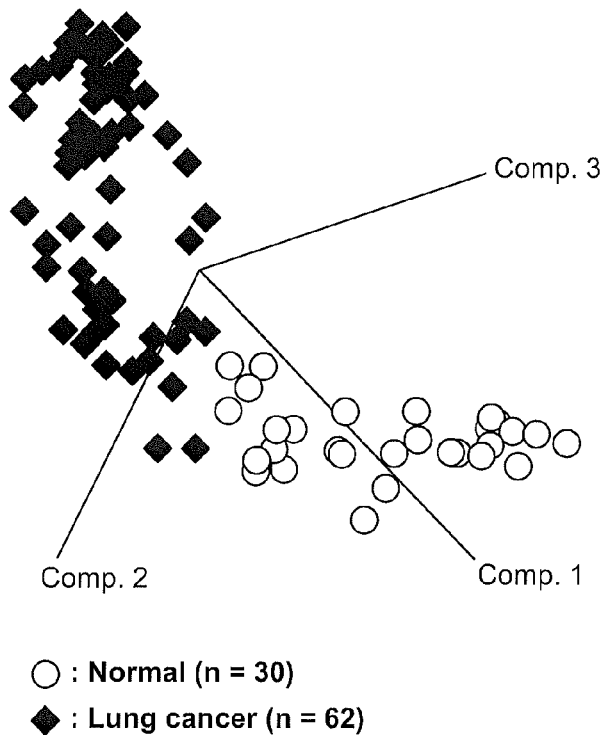
FIG. 8
○ : Normal (n = 30)
◆ : Lung cancer (n = 62)
FIG. 7
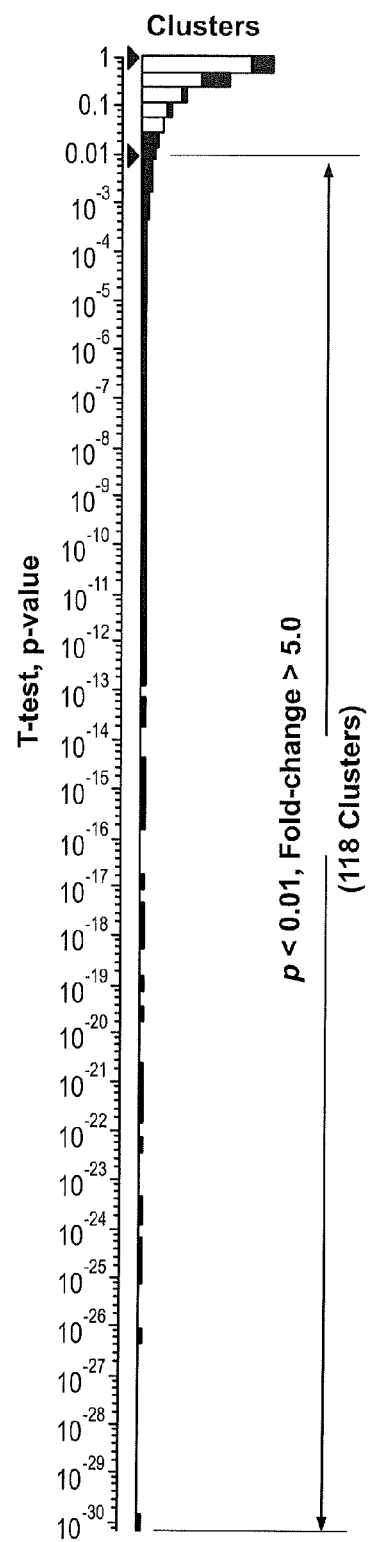

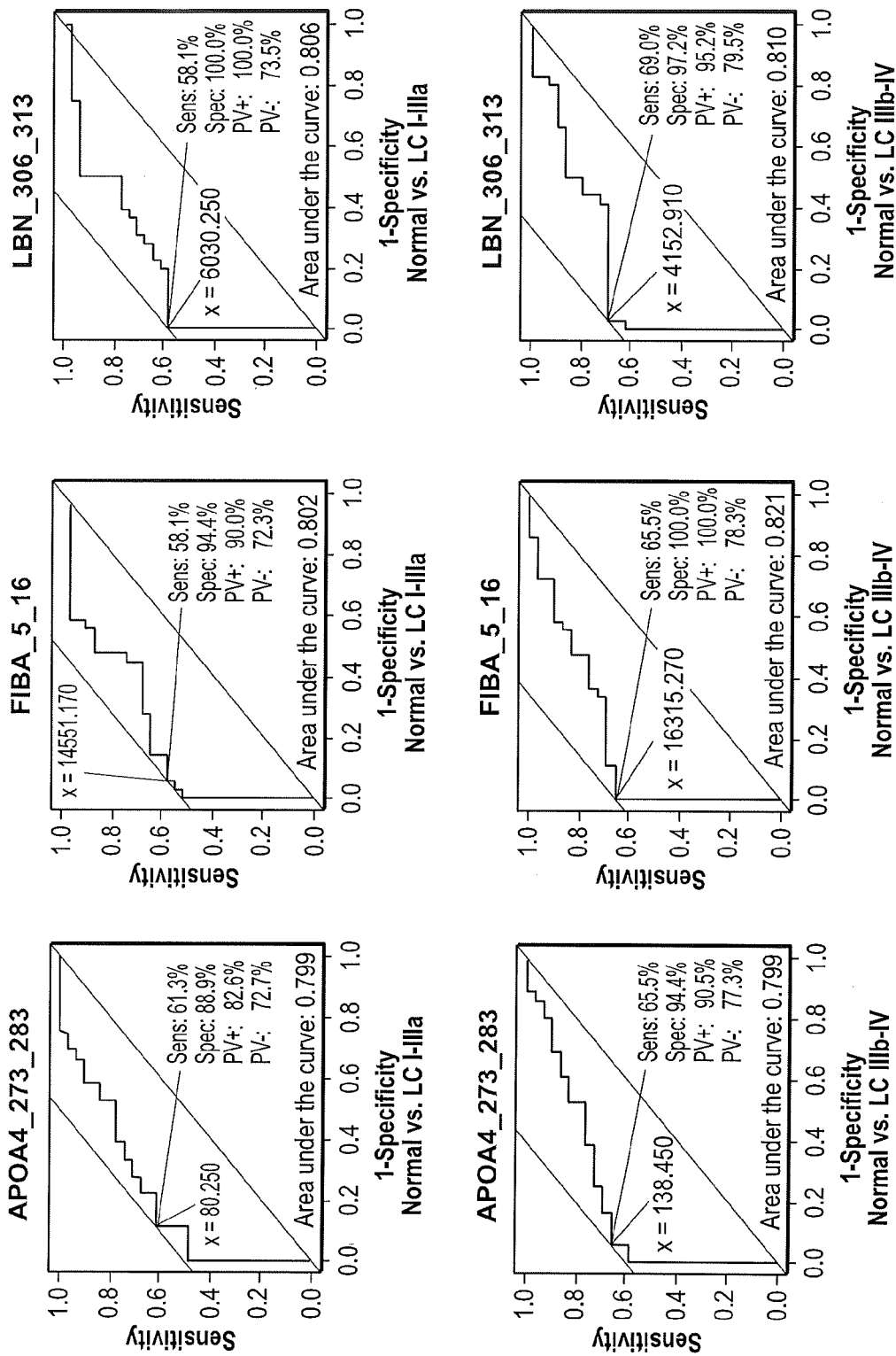

LUNG CANCER DIAGNOSTIC POLYPEPTIDE, METHOD FOR DETECTING LUNG CANCER, AND METHOD FOR EVALUATING THERAPEUTIC EFFECT

This Nonprovisional application claims priority under 35 U.S.C. §119(a) on Patent Application No. 2010-194268 filed in Japan on Aug. 31, 2010, the entire contents of which are hereby incorporated by reference.

TECHNICAL FIELD

The present invention relates to a lung cancer diagnostic polypeptide, a method for detecting lung cancer with use of a lung cancer diagnostic polypeptide, and a method for evaluating a therapeutic effect.

BACKGROUND ART

Lung cancer, which is the leading cause of cancer death in Japan, Europe, and the United States, is refractory. Lung cancer can be divided into small cell lung cancer and non-small cell lung cancer with prevalence rates of 15% and 85%, respectively, and non-small cell lung cancer can be histopathologically classified into three types: adenocarcinoma, squamous cell carcinoma, and large cell carcinoma.

Smoking is still the leading risk factor for lung cancer, but recently the portion of never smoker-related lung cancer (which is mainly categorized as adenocarcinoma) is increasing. Lung cancer patients have an overall 5-year survival rate of only about 15%. This is largely due to the lack of methods for detecting early stage lung cancer, and only 16% of patients are diagnosed with early-stage diseases. Current screening methods such as chest X-ray, sputum cytologic examination, and helical CT have not yet shown their effectiveness in the improvement of mortality of lung cancer.

On the other hand, serum biomarkers for lung cancer have been investigated to achieve early detection of the disease and improve clinical management (see Non-patent Literature 1). Nonetheless, their present clinical usefulness remains limited (see Non-patent Literatures 2 and 3). CEA (carcinoembryonic antigen) and CYFRA (cytokeratin 19 fragment) are elevated in sera from a subset of non-small cell lung cancer patients, and they are clinically available for monitoring the disease status and evaluating the response to the treatments. However, they are not recommended for use in clinical diagnosis (see Non-patent Literature 4), because they have been also found to be associated with other types of diseases such as smoking, lung inflammation, and other types of cancer, and they do not have the sufficient power to detect early-stage lung cancer.

Recently, monitoring the protein expression pattern in clinical specimens by proteomics technologies has offered great opportunities to discover potentially new biomarkers for the diagnosis of cancer. Various proteomic tools such as 2D-DIGE, SELDI-TOF-MS, protein arrays, ICAT, iTRAQ, and MudPIT have been used for differential analysis of various biological samples including cell lysates, serum, and plasma to better understand the molecular basis of cancer pathogenesis and the characterization of disease-associated proteins (see Non-patent Literature 5).

In order to identify minor components in complicated biological samples as putative biomarkers, focused proteomics or targeted proteomics technologies have been especially attracting attention. They involve, for instance, the phosphoproteomics technologies such as IMAC (see Non-patent Literature 6), the cell-surface-capturing (CSC) technology (see Non-patent Literatures 7 and 8), and glycan structure-specific quantification technology IGEL (see Non-patent Literature 9). These methods can circumvent the technological limitations that currently prohibit the sensitive and high-throughput profiling of, in particular, blood proteome samples because of their high complexity and large dynamic range of proteins. Similarly, a branch of proteomics dealing with naturally occurring peptides is often referred to as peptidomics. Direct analysis of peptides produced by processing or degradation of proteins might be useful for detecting biomarker peptides in body fluids (see Non-patent Literature 10). Further, as one sphere of peptidomics, a method for obtaining novel biomarkers with use of mass spectrometry technology has also been proposed (see Non-patent Literature 11).

So far, more than 500 proteases/peptidases are known to be expressed by human cells (see Non-patent Literatures 12 and 13). They function at almost all locations in the body including intracellular region, extracellular matrices, and in blood, involved in activation of other protein functions, degradation, of cellular proteins, and notably tumor progression or suppression (see Non-patent Literatures 14 to 16). Indeed, many matrix metalloproteases are overexpressed in various types of tumor cells, which facilitate construction of favorable microenvironment for tumor cells and promote metastasis (see Non-patent Literature 16).

CITATION LIST

Non-Patent Literature 1
Gail M. H., Muenz L., McIntire K. R., Radovich B., Braunstein G., Brown P. R., Deftos L., Dnistrian A., Dunsmore M., Elashoff R., and et al., *J. Natl. Cancer Inst.* 1988, 80, 97-101.
Non-Patent Literature 2
McCarthy N. J., and Swain S. M., *Cancer J.* 2001, 7, 175-177.
Non-Patent Literature 3
Brundage M. D., Davies D., and Mackillop W. J., *Chest* 2002, 122, 1037-1057.
Non-Patent Literature 4
Sung H. J. and Cho J. Y., *BMB Rep.* 2008, 41, 615-625.
Non-Patent Literature 5
Maurya P., Meleady P., Dowling P., and Clynes M., *Anticancer Res.* 2007, 27, 1247-1255.
Non-Patent Literature 6
Gamez-Pozo A., Sanchez-Navarro I., Nistal M., Calvo E., Madero R., Diaz E., Camafeita E., de Castro J., Lopez J. A., Gonzalez-Baron M., Espinosa E., and Fresno Vara J. A., *PloS One* 2009, 4, e7731.
Non-Patent Literature 7
Wollscheid B., Bausch-Fluck D., Henderson C., O'Brien R., Bibel M., Schiese R., Aebersold R., and Watts J. D., *Nat. Biotechnol.* 2009, 27, 378-386.
Non-Patent Literature 8
Schiese R., Wollscheid B., and Aebersold R., *Mol. Oncol.* 2009, 3, 33-44.
Non-Patent Literature 9
Ueda K., Takami S., Saichi N., Daigo Y., Ishikawa N., Kohno N., Katsumata M., Yamane A., Ota M., Sato T. A., Nakamura Y., and Nakagawa H., *Mol. Cell Proteomics* 2010.
Non-Patent Literature 10
Villanueva J., Nazarian A., Lawlor K., and Tempst P., *Nat. Protoc.* 2009, 4, 1167-1183.
Non-Patent Literature 11
Ueda K., Sato T., Daigo Y., Ishikawa N., Kohno N., Nakamura Y., and Nakagawa H., AACR-JCA 8th Joint Conference: Cancer Genomics, Epigenomics, and the Development of Novel Therapeutics, 2010.

Non-Patent Literature 12
Lopez-Otin C. and Bond J. S., *J. Biol. Chem.* 2008, 283, 30433-30437.
Non-Patent Literature 13
Overall C. M. and Blobel C. P., *Nat. Rev. Mol. Cell Biol.* 2007, 8, 245-257.
Non-Patent Literature 14
Palermo C. and Joyce J. A., *Trends Pharmacol. Sci.* 2008, 29, 22-28.
Non-Patent Literature 15
Lopez-Otin C. and Matrisian L. M., *Nat. Rev. Cancer* 2007, 7, 800-808.
Non-Patent Literature 16
Egeblad M. and Werb Z., *Nat. Rev. Cancer* 2002, 2, 161-174.

SUMMARY OF INVENTION

Technical Problem

CEA, CYFRA, SCC, SLC, NSE, and ProGRP are clinically used as tumor markers for both lung cancer diagnosis and prognosis, which can be measured in serum. Especially, regarding the diagnosis of non-small cell lung cancer, CEA, CYFRA, SCC, and SLX are frequently utilized although only very limited sensitivity and specificity for detecting early-stage lung cancer have been certified.

Therefore, there has been a strong demand for the development of novel biomarkers that can be applied in non-small cell lung cancer diagnosis, in particular, at the early-stage lung cancer (Stage-0, Ia, Ib, IIa, or IIb, based on Union for International Cancer Control (UICC) cancer staging).

The present invention has been made in order to address the foregoing issues, and to provide more sensitive and specific biomarkers for the early detection of non-small cell lung cancer, which would lead to the drastic reduction of incidence and mortality caused by lung cancer.

Solution to Problem

Aberrant activation or inactivation of proteases and peptidases result in the production of digested peptide fragments well reflecting the tumor progression or tumor-associated responses. Thus, peptidomic profiling of human serum or human plasma is a promising tool for the discovery of novel tumor markers.

The inventors diligently studied based on the foregoing supposition. As a result, the high throughput peptidome enrichment by gel filtration and the comprehensive quantification analysis by the mass spectrometer revealed that the concentration of a set of peptides were significantly elevated in sera of lung cancer patients, even at the very early stages. Thus, the inventors accomplished the present invention.

In order to solve the foregoing problems, a lung cancer diagnostic polypeptide according to the present invention consists of an amino acid sequence represented by any one of SEQ ID NOS: 1 to 19.

In order to solve the foregoing problems, a detecting method for lung cancer according to the present invention includes the step of detecting or measuring at least one lung cancer diagnostic polypeptide selected from a group of lung cancer diagnostic polypeptides consisting of amino acid sequences represented by SEQ ID NOS: 1 to 19 in a sample collected from a living organism.

A method for evaluating a therapeutic effect in a lung cancer patient according to the present invention includes the steps of: (i) detecting or measuring at least one lung cancer diagnostic polypeptide selected from a group of lung cancer diagnostic polypeptides consisting of amino acid sequences represented by SEQ ID NOS: 1 to 19 in a sample collected from a living organism before and after treatments; and (ii) comparing results acquired from the respective samples.

Advantageous Effects of Invention

Use of a lung cancer diagnostic polypeptide according to the present invention makes it possible to detect lung cancer more sensitively and specifically from the biological samples, compared to previous methods. Therefore, the lung cancer diagnostic polypeptides according to the present invention can be used as novel lung cancer biomarkers.

BRIEF DESCRIPTION OF DRAWINGS

FIG. 7 is a hierarchical chart of clusters according to t-test p-values between a group of normal healthy persons and a group of lung cancer patients.

FIG. 8 shows a result of principal component analysis performed on candidate biomarker peptides.

FIG. 11 shows ROC curves showing results of relative quantification analysis.

DESCRIPTION OF EMBODIMENTS

1. Lung Cancer Diagnostic Polypeptide

Figure 1:
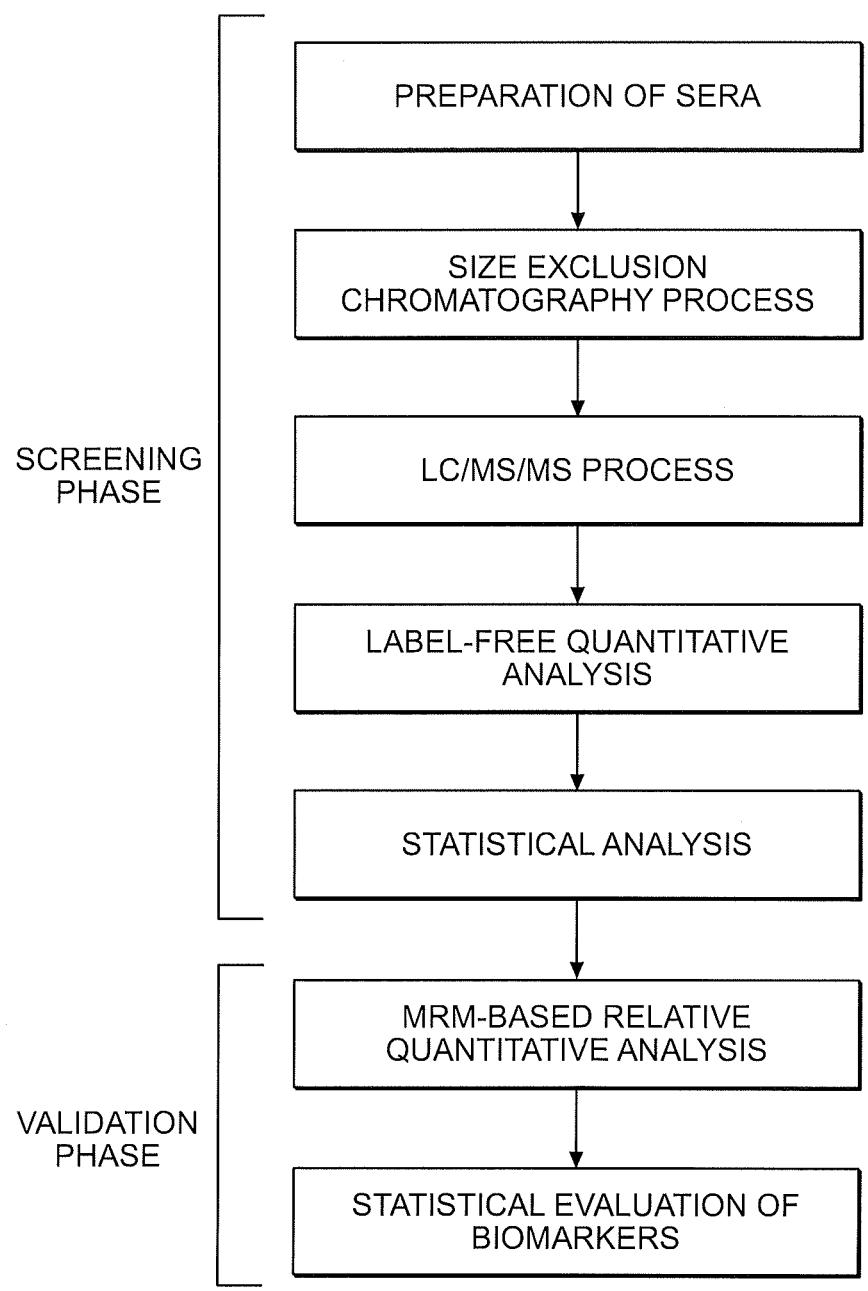
FIG. 1 schematically shows the method for screening biomarker peptides.

A lung cancer diagnostic polypeptide according to the present invention is a polypeptide consisting of an amino acid sequence represented by any one of SEQ ID NOS: 1 to 19.

Such polypeptides are found more largely in sera from lung cancer patients than in those from normal healthy persons. Therefore, lung cancer can be detected by measuring the concentrations of lung cancer diagnostic polypeptides according to the present invention in sera and comparing them to the concentrations of such polypeptides in normal healthy persons. That is, the lung cancer diagnostic polypeptides according to the present invention can be used as biomarkers for use in lung cancer detection.

The term "lung cancer" here refers to non-small cell lung cancer including human adenocarcinoma (lung adenocarcinoma), squamous cell carcinoma, and large cell carcinoma. The lung cancer diagnostic polypeptides according to the present invention are especially effective, in particular, for detecting adenocarcinoma.

The amino acid sequence represented by SEQ ID NO: 1 is a sequence of the 613th to 624th amino acid residues as counted from the N terminal of a human amiloride-sensitive cation channel 4 (ACCN4) protein. A polypeptide consisting of this amino acid sequence is herein referred to as "ACCN4 613-624".

The amino acid sequences represented by SEQ ID NOS: 2 to 5 are a sequence of the 271st to 283rd amino acid residues, a sequence of the 268th to 284th amino acid residues, a sequence of the 260th to 284th amino acid residues, and a sequence of the 273rd to 283rd amino acid residues, respectively, as counted from the N terminal of a human apolipoprotein A-IV (APOA4). Polypeptides consisting of these amino acid sequences are herein referred to as "APOA4 271-283", "APOA4 268-284", "APOA4 260-284", and "APOA4 273-283", respectively.

The amino acid sequence represented by SEQ ID NO: 6 is a sequence of the 194th to 214th amino acid residues as counted from the N terminal of a human apolipoprotein E (APOE). A polypeptide consisting of this amino acid sequence is herein referred to as "APOE 194-214".

The amino acid sequences represented by SEQ ID NOS: 7 to 18 are a sequence of the 1st to 16th amino acid residues, a sequence of the 7th to 15th amino acid residues, a sequence of the 7th to 16th amino acid residues, a sequence of the 2nd to 16th amino acid residues, a sequence of the 5th to 15th amino acid residues, a sequence of the 5th to 16th amino acid residues, a sequence of the 6th to 15th amino acid residues, a sequence of the 6th to 16th amino acid residues, a sequence of the 4th to 15th amino acid residues, a sequence of the 4th to 16th amino acid residues, a sequence of the 3rd to 15th amino acid residues, and a sequence of the 3rd to 16th amino acid residues, respectively, as counted from the N terminal of a human fibrinogen alpha chain (FIBA). Polypeptides consisting of these amino acid sequences are herein referred to as "FIBA 1-16", "FIBA 7-15", "FIBA 7-16", "FIBA 2-16", "FIBA 5-15", "FIBA 5-16", "FIBA 6-15", "FIBA 6-16", "FIBA 4-15", "FIBA 4-16", "FIBA 3-15", and "FIBA 3-16", respectively.

The amino acid sequence represented by SEQ ID NO: 19 is a sequence of the 306th to 313th amino acid residues as counted from the N terminal of a human limbin protein. A polypeptide consisting of this amino acid sequence is herein referred to as "LBN 306-313".

Table 1 shows the respective amino acid sequences of these lung cancer diagnostic polypeptides.

TABLE 1

| Lung cancer diagnostic polypeptides | Amino acid sequences |
| --- | --- |
| ACCN4 613-624 (SEQ ID NO: 1) | CPSLGRAEGGGV |
| APOA4 271-283 (SEQ ID NO: 2) | ELGGHLDQQVEEF |
| APOA4 268-284 (SEQ ID NO: 3) | SLAELGGHLDQQVEEFR |
| APOA4 260-284 (SEQ ID NO: 4) | GNTEGLQKSLAELGGHLDQQVEEFR |
| APOA4 273-283 (SEQ ID NO: 5) | GGHLDQQVEEF |
| APOE 194-214 (SEQ ID NO: 6) | TVGSLAGQPLQERAQAWGERL |
| FIBA 1-16 (SEQ ID NO: 7) | ADSGEGDFLAEGGGVR |
| FIBA 7-15 (SEQ ID NO: 8) | DFLAEGGGV |
| FIBA 7-16 (SEQ ID NO: 9) | DFLAEGGGVR |
| FIBA 2-16 (SEQ ID NO: 10) | DSGEGDFLAEGGGVR |
| FIBA 5-15 (SEQ ID NO: 11) | EGDFLAEGGGV |
| FIBA 5-16 (SEQ ID NO: 12) | EGDFLAEGGGVR |

TABLE 1-continued

| Lung cancer diagnostic polypeptides | Amino acid sequences |
| --- | --- |
| FIBA 6-15 (SEQ ID NO: 13) | GDFLAEGGGV |
| FIBA 6-16 (SEQ ID NO: 14) | GDFLAEGGGVR |
| FIBA 4-15 (SEQ ID NO: 15) | GEGDFLAEGGGV |
| FIBA 4-16 (SEQ ID NO: 16) | GEGDFLAEGGGVR |
| FIBA 3-15 (SEQ ID NO: 17) | SGEGDFLAEGGGV |
| FIBA 3-16 (SEQ ID NO: 18) | SGEGDFLAEGGGVR |
| LBN 306-313 (SEQ ID NO: 19) | FLLSLVLT |

Among these lung cancer diagnostic polypeptides, ACCN4 613-624, APOA4 260-284, APOA4 273-283, FIBA 1-16, FIBA 2-16, FIBA 5-16, FIBA 6-15, FIBA 6-16, FIBA 4-16, FIBA 3-15, FIBA 3-16, and LBN 306-313 show big significant differences between the concentrations in sera from normal healthy persons and the concentrations in sera from lung cancer patients and therefore are more preferable as biomarkers for detecting lung cancer.

Furthermore, APOA4 273-283, FIBA 5-16, and LBN 306-313 are superior in sensitivity and specificity at operable stages of lung cancer (stages I. II. and IIIa) and therefore are especially preferable, in particular, as biomarkers for detecting lung cancer at operable stages.

From the point of view of being found more largely in sera from lung cancer patients than in sera from normal healthy persons, those compounds designated ID_001 to ID_118 in Table 2 can also be used as biomarkers for detecting lung cancer. Those compounds listed in Table 2, which are compounds derived from human serum, are peptides having molecular weights shown in correspondence therewith. It should be noted that those values of molecular weight, m/z, RT (retention time), and Charge shown in Table 2 are values identified by a measurement method to be described below in Example 3. Further, when the compounds are peptides or modified peptides, their amino acid sequences can be identified by a measurement method to be described below in Example 4. It should be noted that judging from the numbers of charges during ionization and the molecular weights, those compounds designated ID_001 to ID_118 are presumed to be peptides or modified peptides.

TABLE 2

| Compounds | Molecular weight | m/z | RT | Charge |
| --- | --- | --- | --- | --- |
| ID_001 | 1615.61 | 808.81 | 57.5 | 2 |
| ID_002 | 1205.53 | 603.77 | 50.7 | 2 |
| ID_003 | 1207.56 | 604.79 | 50.6 | 2 |
| ID_004 | 1049.45 | 525.73 | 62.8 | 2 |
| ID_005 | 1019.48 | 510.74 | 49.9 | 2 |
| ID_006 | 1466.63 | 734.32 | 54.3 | 2 |
| ID_007 | 904.45 | 453.23 | 39.0 | 2 |
| ID_008 | 1193.51 | 597.76 | 63.2 | 2 |
| ID_009 | 1535.68 | 768.85 | 53.0 | 2 |
| ID_010 | 1349.60 | 675.81 | 52.3 | 2 |
| ID_011 | 863.39 | 432.70 | 62.6 | 2 |
| ID_012 | 1106.48 | 554.25 | 63.5 | 2 |
| ID_013 | 1464.60 | 733.31 | 54.5 | 2 |
| ID_014 | 1535.68 | 512.90 | 53.0 | 3 |
| ID_015 | 1262.57 | 632.29 | 52.1 | 2 |
| ID_016 | 1357.45 | 453.49 | 64.5 | 3 |
| ID_017 | 1057.39 | 529.70 | 60.3 | 2 |
| ID_018 | 1429.59 | 715.80 | 56.7 | 2 |
| ID_019 | 1102.37 | 552.19 | 62.8 | 2 |
| ID_020 | 1361.46 | 681.74 | 64.5 | 2 |
| ID_021 | 1544.59 | 773.30 | 57.6 | 2 |
| ID_022 | 1459.54 | 730.78 | 67.2 | 2 |
| ID_023 | 1464.63 | 489.22 | 54.2 | 3 |

TABLE 2-continued

| Compounds | Molecular weight | m/z | RT | Charge |
|---|---|---|---|---|
| ID_024 | 1721.48 | 574.83 | 57.1 | 3 |
| ID_025 | 1377.43 | 689.72 | 71.2 | 2 |
| ID_026 | 1449.46 | 725.74 | 74.0 | 2 |
| ID_027 | 1101.51 | 551.76 | 64.1 | 2 |
| ID_028 | 1175.50 | 588.76 | 63.2 | 2 |
| ID_029 | 1517.68 | 759.85 | 60.0 | 2 |
| ID_030 | 1397.54 | 699.78 | 74.9 | 2 |
| ID_031 | 1464.65 | 733.33 | 56.5 | 2 |
| ID_032 | 1076.62 | 539.27 | 52.3 | 2 |
| ID_033 | 1076.51 | 539.26 | 49.1 | 2 |
| ID_034 | 1158.44 | 580.23 | 63.5 | 2 |
| ID_035 | 1325.57 | 663.79 | 64.5 | 2 |
| ID_036 | 1242.42 | 622.22 | 63.2 | 2 |
| ID_037 | 1219.48 | 610.74 | 71.2 | 2 |
| ID_038 | 1513.54 | 505.52 | 54.2 | 3 |
| ID_039 | 920.42 | 461.22 | 61.8 | 2 |
| ID_040 | 2473.91 | 1237.96 | 76.8 | 2 |
| ID_041 | 1785.86 | 596.29 | 61.1 | 3 |
| ID_042 | 970.36 | 486.19 | 65.5 | 2 |
| ID_043 | 1014.27 | 508.14 | 49.8 | 2 |
| ID_044 | 845.38 | 423.70 | 62.6 | 2 |
| ID_045 | 1444.46 | 723.24 | 74.1 | 2 |
| ID_046 | 1239.48 | 620.75 | 76.8 | 2 |
| ID_047 | 1615.64 | 539.55 | 57.4 | 3 |
| ID_048 | 907.46 | 454.74 | 39.0 | 2 |
| ID_049 | 1155.39 | 578.70 | 63.5 | 2 |
| ID_050 | 973.33 | 487.67 | 61.8 | 2 |
| ID_051 | 1049.46 | 525.74 | 65.0 | 2 |
| ID_052 | 2009.98 | 1006.00 | 75.6 | 2 |
| ID_053 | 1449.46 | 725.74 | 74.9 | 2 |
| ID_054 | 3260.50 | 816.13 | 45.6 | 4 |
| ID_055 | 1246.59 | 624.30 | 63.2 | 2 |
| ID_056 | 1187.56 | 594.79 | 61.7 | 2 |
| ID_057 | 798.30 | 400.16 | 52.0 | 2 |
| ID_058 | 1240.46 | 414.49 | 61.7 | 3 |
| ID_059 | 912.30 | 457.16 | 62.6 | 2 |
| ID_060 | 2658.28 | 887.10 | 16.6 | 3 |
| ID_061 | 2119.22 | 808.81 | 74.1 | 3 |
| ID_062 | 1254.46 | 603.77 | 50.5 | 3 |
| ID_063 | 1069.56 | 604.79 | 49.6 | 2 |
| ID_064 | 1377.55 | 525.73 | 75.3 | 2 |
| ID_065 | 943.35 | 510.74 | 61.9 | 2 |
| ID_066 | 1066.72 | 734.32 | 112.0 | 2 |
| ID_067 | 1664.54 | 453.23 | 57.4 | 3 |
| ID_068 | 1377.54 | 597.76 | 74.0 | 2 |
| ID_069 | 1257.61 | 768.85 | 52.2 | 2 |
| ID_070 | 1324.54 | 675.81 | 69.6 | 2 |
| ID_071 | 1306.50 | 432.70 | 74.0 | 2 |
| ID_072 | 1228.49 | 554.25 | 66.7 | 2 |
| ID_073 | 972.35 | 733.31 | 58.3 | 2 |
| ID_074 | 1448.47 | 512.90 | 72.9 | 2 |
| ID_075 | 1205.57 | 632.29 | 53.5 | 2 |
| ID_076 | 1231.58 | 453.49 | 56.5 | 2 |
| ID_077 | 2658.28 | 529.70 | 16.6 | 4 |
| ID_078 | 1022.50 | 715.80 | 49.8 | 2 |
| ID_079 | 1123.52 | 552.19 | 63.5 | 2 |
| ID_080 | 2529.10 | 681.74 | 76.4 | 2 |
| ID_081 | 1209.48 | 773.30 | 55.3 | 2 |
| ID_082 | 1359.66 | 730.78 | 71.4 | 2 |
| ID_083 | 1263.39 | 489.22 | 55.4 | 2 |
| ID_084 | 1412.59 | 574.83 | 73.5 | 2 |
| ID_085 | 1284.53 | 689.72 | 65.7 | 2 |
| ID_086 | 1413.57 | 725.74 | 66.3 | 2 |
| ID_087 | 1631.63 | 551.76 | 59.7 | 2 |
| ID_088 | 1204.54 | 588.76 | 68.2 | 2 |
| ID_089 | 1517.67 | 759.85 | 54.7 | 2 |
| ID_090 | 1060.40 | 699.78 | 60.2 | 2 |
| ID_091 | 1173.60 | 733.33 | 80.0 | 2 |
| ID_092 | 1350.59 | 539.27 | 58.0 | 2 |
| ID_093 | 1808.12 | 539.26 | 50.4 | 3 |
| ID_094 | 1420.66 | 580.23 | 51.9 | 2 |
| ID_095 | 1349.61 | 663.79 | 52.2 | 3 |
| ID_096 | 1203.56 | 622.22 | 80.8 | 2 |
| ID_097 | 1615.72 | 610.74 | 53.0 | 3 |
| ID_098 | 1014.39 | 505.52 | 65.5 | 2 |
| ID_099 | 1499.69 | 461.22 | 60.3 | 2 |
| ID_100 | 2502.23 | 1237.96 | 73.5 | 3 |
| ID_101 | 1419.63 | 596.29 | 61.0 | 2 |
| ID_102 | 4186.62 | 486.19 | 74.0 | 3 |
| ID_103 | 1397.56 | 508.14 | 73.5 | 2 |
| ID_104 | 1410.73 | 423.70 | 33.6 | 2 |
| ID_105 | 1411.55 | 723.24 | 69.8 | 2 |
| ID_106 | 1313.68 | 620.75 | 41.1 | 3 |
| ID_107 | 1468.69 | 539.55 | 55.8 | 2 |
| ID_108 | 2266.18 | 454.74 | 65.6 | 3 |
| ID_109 | 2961.78 | 578.70 | 35.8 | 5 |
| ID_110 | 2355.18 | 487.67 | 65.1 | 3 |
| ID_111 | 1124.47 | 525.74 | 54.6 | 2 |
| ID_112 | 1129.42 | 1006.00 | 65.0 | 2 |
| ID_113 | 1349.63 | 725.74 | 53.1 | 2 |
| ID_114 | 1464.65 | 816.13 | 53.0 | 2 |
| ID_115 | 885.44 | 624.30 | 61.2 | 2 |
| ID_116 | 2713.43 | 594.79 | 43.2 | 4 |
| ID_117 | 1551.67 | 400.16 | 63.7 | 2 |
| ID_118 | 1613.81 | 414.49 | 62.8 | 3 |

That is, lung cancer can also be detected by detecting or measuring, in serum collected from a subject, a compound having a molecular weight shown in Table 2.

It should be noted that among the compounds ID_001 to ID_118, at least ID_002 (FIBA 5-16), ID_004 (FIBA 5-15), ID_005 (FIBA 7-16), ID_007 (LBN 306-313), ID_008 (FIBA 3-15), ID_009 (FIBA 1-16), ID_010 (FIBA 3-16), ID_011 (FIBA 7-15), ID_012 (FIBA 4-15), ID_013 (FIBA 2-16), ID_015 (FIBA 4-16), ID_023 (FIBA 2-16), ID_027 (ACCN4 613-624), ID_031 (FIBA 2-16), ID_032 (FIBA 6-16), ID_033 (FIBA 6-16), ID_039 (FIBA 6-15), ID_051 (FIBA 5-15), ID_064 (APOA4 260-284), ID_069 (APOA4 273-283), ID_075 (FIBA 5-16), ID_085 (APOA4 268-284), ID_093 (FIBA 5-16), ID_099 (APOA4 271-283), ID_108 (APOE 194-214), ID_113 (FIBA 3-16), and ID_114 (FIBA 2-16) are peptides, whose amino acid sequences have been identified by database search, categorized into any one of the polypeptides shown in Table 1.

2. Method for Detecting Lung Cancer

A method for detecting lung cancer according to the present invention needs only include the step of detecting or measuring, in a sample collected from a living organism, at least one lung cancer diagnostic polypeptide selected from the group of lung cancer diagnostic polypeptides consisting of the amino acid sequences represented by SEQ ID NOS: 1 to 19. Other specific steps and apparatuses and instruments that are used are not particularly limited.

The phrase "measuring a lung cancer diagnostic polypeptide" here is intended to mean measuring the amount or concentration of a lung cancer diagnostic polypeptide present in a biological sample or a sample obtained by purifying such a biological sample.

An example of the detection method of the present invention can detect lung cancer by measuring the amount of at least one lung cancer diagnostic polypeptide in a biological sample from both a subject and controls (normal healthy persons), and comparing the amounts. Especially, if a significant difference is found between the amount of lung cancer diagnostic polypeptide in the biological sample from a subject and the normal level, the subject could be diagnosed as lung-cancer or highly suspected as lung cancer. The amount of lung cancer diagnostic polypeptide in the biological sample from the normal healthy person may be one measured in advance. Alternatively, it is also possible to measure in advance the amounts of lung cancer diagnostic polypeptide in biological samples from normal healthy persons and define the normal range of concentration.

The term "sample" here indicates any biological specimens collected from a living organism (human), in which the lung cancer diagnostic polypeptides are detectable. Usable examples of such samples include blood, serum, plasma, etc. Among them, serum and plasma are preferable.

A method for detecting or measuring a lung cancer diagnostic polypeptide is not particularly limited as long as it can quantitatively or semiquantitatively determine the amount of lung cancer diagnostic polypeptide present or can determine the presence or absence of a lung cancer diagnostic polypeptide. Usable examples of such methods include immunological techniques such as ELISA, western blotting, and immunoprecipitation, as well as mass spectrometry. Among them, mass spectrometry is preferable for the following reasons. Mass spectrometry with a mass spectrometer eliminates the need to produce a specific antibody and therefore can easily detect or measure a lung cancer diagnostic polypeptide. Further, mass spectrometry with a mass spectrometer is superior in sensitivity and precision and therefore ensures a more accurate determination. Furthermore, use of a multichannel mass spectrometer capable of simultaneous multicomponent analysis makes it possible to detect or measure two or more lung cancer diagnostic polypeptides at once. Use of two or more lung cancer diagnostic polypeptides makes it possible to more accurately determine whether or not the subject is lung-cancer-stricken. Alternatively, a combination of two or more lung cancer diagnostic polypeptides makes it possible to more accurately determine in which stage the lung cancer currently is. Furthermore, this makes it possible to simultaneously measure biomarkers for diseases other than lung cancer, thus making it possible to attempt to detect various diseases at once. Further, for more precise detection, it is preferable that a tandem mass spectrometer (MS/MS) be used. A mass spectrometer that is used in the detection method of the present invention is not particularly limited as long as it is capable of quantitative determination. Usable examples of such mass spectrometers include conventionally publicly-known types of mass spectrometer such as a quadrupole mass spectrometer and a time-of-flight mass spectrometer.

It is preferable that a sample that is used for detection or measurement of a lung cancer diagnostic polypeptide be subjected to heat treatment after being collected from a living organism and before the detection or measurement of a lung cancer diagnostic polypeptide. Heat treatment of the sample deactivates proteases contained in the sample, thereby preventing a lung cancer diagnostic polypeptide from being degraded before the detection and measurement. Possible examples of heat treatment include treatment of ten minutes at 100° C. Alternatively, the degradation of peptides by proteases may be prevented by subjecting the sample to acid modification or an organic solvent precipitation method instead of heat treatment. In the case of acid modification, for example, it is only necessary to use, as the sample for use in detection and measurement, a supernatant obtained by precipitating only proteins by heating at 60° C. in the presence of 1% trifluoroacetic acid. Alternatively, in the case of an organic solvent precipitation method, for example, it is only necessary to use, as the sample for use in detection and measurement, a supernatant similarly obtained by precipitating only proteins by addition of an amount of an organic solvent, such as acetone and acetonitrile, five to ten times as large the amount of serum. From the point of view of efficiency, it is preferable that heat treatment be simply carried out.

It is preferable that a sample that is used for detection or measurement of a lung cancer diagnostic polypeptide be concentrated as a fraction containing a lung cancer diagnostic polypeptide by gel filtration chromatography (size exclusion chromatography) before being subjected to mass spectrometry, and that detection or measurement of a lung cancer diagnostic polypeptide in this fraction be carried out. This makes it possible to subject the sample to mass spectrometry in a single step from a blood sample, i.e., makes it possible to skip all the steps, such as tryptic digestion, that are essential to MS analysis of proteins. Therefore, the detection or measurement of a lung cancer diagnostic polypeptide can be easily and quickly carried out. Further, the gel filtration chromatographic process does not require poisonous and deleterious materials such as an organic solvent and a strong acid and, as such poses only a low risk of health hazards on persons engaged, thus allowing health professionals such as clinical technologists to execute preprocessing. Furthermore, the gel filtration chromatographic process is highly effective in excluding polymers such as proteins, thus enhancing the reproducibility of the subsequent step of mass spectrometric detection.

A fraction that is collected as a fraction containing a lung cancer diagnostic polypeptide, as long as it contains a lung cancer diagnostic polypeptide, is not limited in range of molecular weights of the polypeptide. For example, it is only necessary to collect a fraction containing peptides whose molecular weights are not less than 1,000 (Da) and not more than 5,000 (Da).

Disease biomarker candidate proteins and peptides that can be applied to serum and plasma have so far been identified by various approaches, but their clinical applications require methods that have a wide dynamic range and allow accurate processing of multiple samples. Most of such methods have been borne by ELISA systems using specific antibodies, but it is difficult to establish a specific antibody that can be used in an ELISA system. Most of the time, it is difficult to corroborate disease biomarkers in serum and plasma and carry out an experiment for further, evidence.

On the other hand, a biomarker for use in lung cancer diagnosis and a method for detecting lung cancer according to the present invention allow accurate processing of multiple samples without producing a specific antibody and allow detection of lung cancer with high sensitivity.

3. Method for Evaluating a Therapeutic Effect in a Lung Cancer Patient

A method for evaluating a therapeutic effect in a lung cancer patient according to the present invention needs only include the steps of: (i) detecting or measuring, in a sample collected from a living organism before treatment and a sample collected from the living organism after treatment, at least one lung cancer diagnostic polypeptide selected from the group of lung cancer diagnostic polypeptides consisting of the amino acid sequences represented by SEQ ID NOS: 1 to 19; and (ii) comparing results detected in the respective samples. Other specific steps and apparatuses and instruments that are used are not particularly limited.

An example of the evaluation method of the present invention can evaluate a therapeutic effect on lung cancer by measuring in advance the amount of at least one lung cancer diagnostic polypeptide in a biological sample from a lung cancer patient before the start of treatment, measuring the amount of the lung cancer diagnostic polypeptide in the same patient after the start of treatment, and comparing the amounts. Specifically, if it is found, as a result of the comparison, that the amount of the lung cancer diagnostic polypeptide after the start of treatment comes close to the amount of the lung cancer diagnostic polypeptide in a biological sample from a normal healthy person and that there is a significant difference between the amounts (before and after the start of treatment), it can be judged that the treatment has had a therapeutic effect on the patient.

It should be noted that the preparation and purification of a biological sample for use in detection or measurement of a lung cancer diagnostic polypeptide and the method for detecting or the method for measuring a lung cancer diagnostic polypeptide can be described with reference to the description of <2. Method for Detecting Lung Cancer> above.

The method for detecting lung cancer according to the present invention preferably includes detecting or measuring at least a lung cancer diagnostic polypeptide consisting of the amino acid sequence represented by SEQ ID NO: 5, 12, or 19.

Further, the method for detecting lung cancer according to the present invention preferably includes detecting or measuring the at least one lung cancer diagnostic polypeptide by mass spectrometry.

Further, the method for detecting lung cancer according to the present invention is preferably configured such that the step includes obtaining a lung cancer diagnostic polypeptide fraction by subjecting the sample to gel filtration chromatography and detecting or measuring, in the fraction thus obtained, the at least one lung cancer diagnostic polypeptide.

Further, the method for detecting lung cancer according to the present invention may include detecting or measuring at once two or more lung cancer diagnostic polypeptides selected from the group of lung cancer diagnostic polypeptides.

Further, the method for detecting lung cancer according to the present invention is preferably configured such that the sample is, blood, serum, or plasma.

Further, the method for detecting lung cancer according to the present invention is preferably configured such that the sample is subjected to heat treatment prior to the step.

Examples are given below to describe the embodiments of the present invention further in detail. Of course, the present invention is not limited to the examples below, and the details of the present invention can take various aspects. Furthermore, the present invention is not limited to the description of the embodiments above, but may be altered by a skilled person within the scope of the claims. An embodiment based on a proper combination of technical means disclosed in different embodiments is encompassed in the technical scope of the present invention. Further, all the documents cited in this specification are used as references.

EXAMPLES

In the examples below, the term "lung cancer" refers to lung adenocarcinoma unless otherwise noted.

Prior to a detailed description of the examples, the workflow of screening of lung cancer diagnostic polypeptides according to the present invention is schematically described with reference to FIG. 1.

In the screening of lung cancer diagnostic polypeptides according to the present invention, first, sera for use in screening were prepared by collecting sera from a plurality of lung cancer patients and normal healthy persons and treating the sera with heat (Examples 1 and 2). Then, fractions with particular molecular weights were collected by subjecting each of the sera for use in screening to size exclusion chromatography (Example 2). The fractions thus collected were subjected to LC/MS/MS, whereby peptide components were extracted from the fractions (Examples 3 and 4). The peptide components thus extracted were subjected to label-free quantification analysis (Example 3). Lung cancer patient-specific peptides were selected by comparing data from the lung cancer patients with data from the normal healthy persons and performing statistical analysis (Example 3). This is the end of the screening phase. In the validation phase, for each of the peptides thus selected, MRM (Multiple Reaction Monitoring)-based relative quantification analysis was performed on sera from other lung cancer patients and normal healthy persons (Example 5). Each of the peptides was evaluated by performing statistical analysis of the results thus obtained (Example 6). In this way, biomarkers for use in detection of lung cancer were identified. These examples are described in detail below.

Example 1

Preparation of Serum

Human serum samples were obtained with informed consent from 122 patients with lung adenocarcinoma (stage I to IV) at Hiroshima University Hospital. Serum samples as normal controls were also obtained with informed consent from 30 healthy volunteers who received medical checkup at Hiroshima NTT Hospital and 36 from Kochi University Hospital.

Serum was collected using standard protocol from whole blood by centrifugation (at 1500×g for 10 min.) and stored at −80° C.

Example 2

Collection of Peptidome Fraction

All serum samples were frozen and thawed once and immediately incubated at 100° C. for ten minutes after four times dilution with proteomics grade water for the prevention of degradation of components in serum by proteases and peptidases and the avoidance of aggregation of proteins during heat treatment. Following filtration with Spin-X 0.45 μm spin filters, 10 μl of samples were loaded into a 10/300 Superdex peptide column (GE Healthcare) coupled with a Prominence HPLC system (Shimadzu). The samples were introduced into HPLC in the constant flow of 100 mM ammonium acetate (at a flow rate of 0.5 ml/min). The samples that had passed through the column were measured for UV absorption at 280 nm. The result is shown in FIG. 2.

Figure 2:
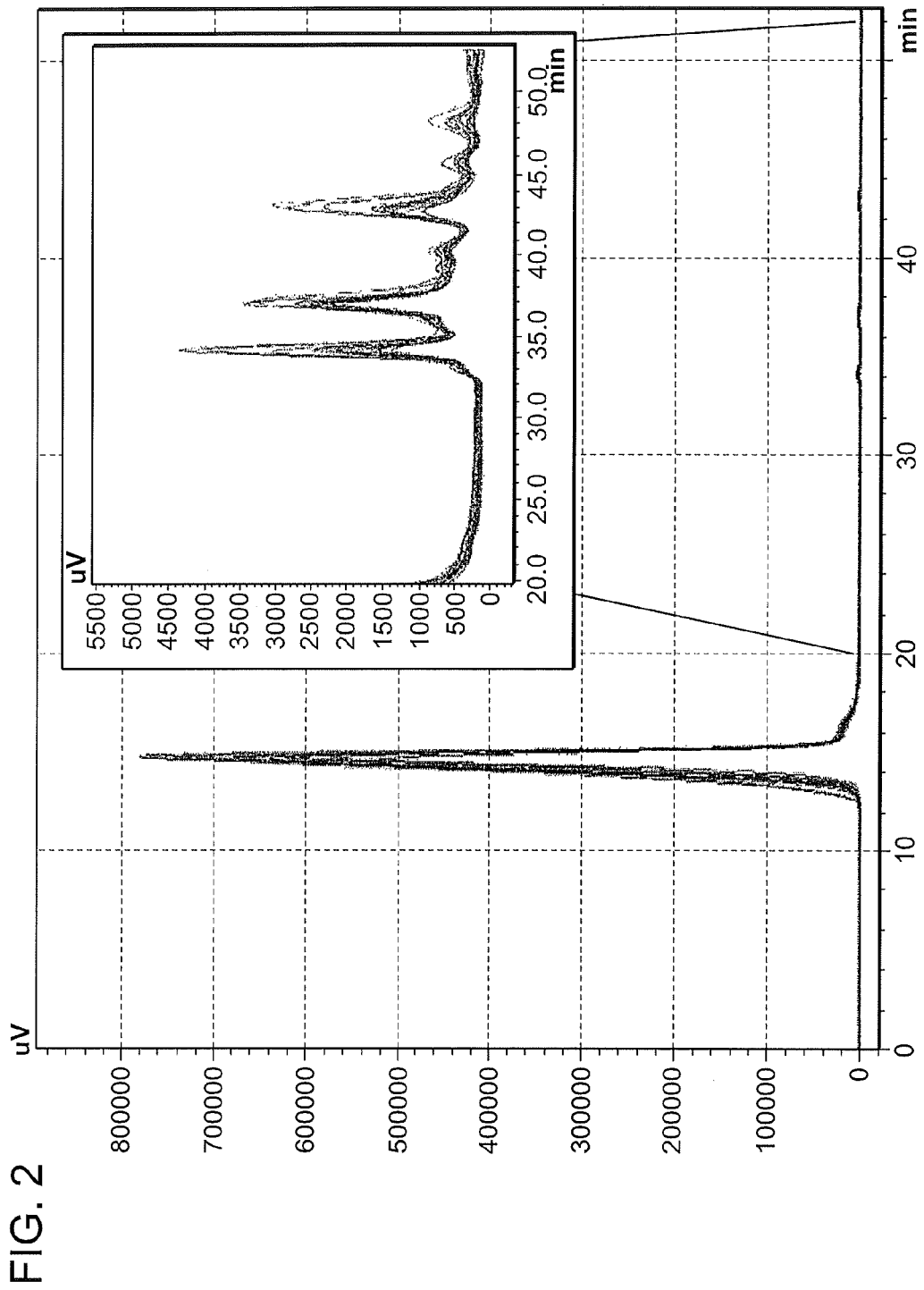
FIG. 2 shows the representative merged spectra obtained as the result of serum peptidome enrichment by gel filtration chromatography on the HPLC.

FIG. 2 shows merged gel filtration HPLC spectra from 16 individual serum samples. As shown in FIG. 2, the gel filtration HPLC resulted in highly reproducible separation of serum proteins and peptides.

Figure 3:
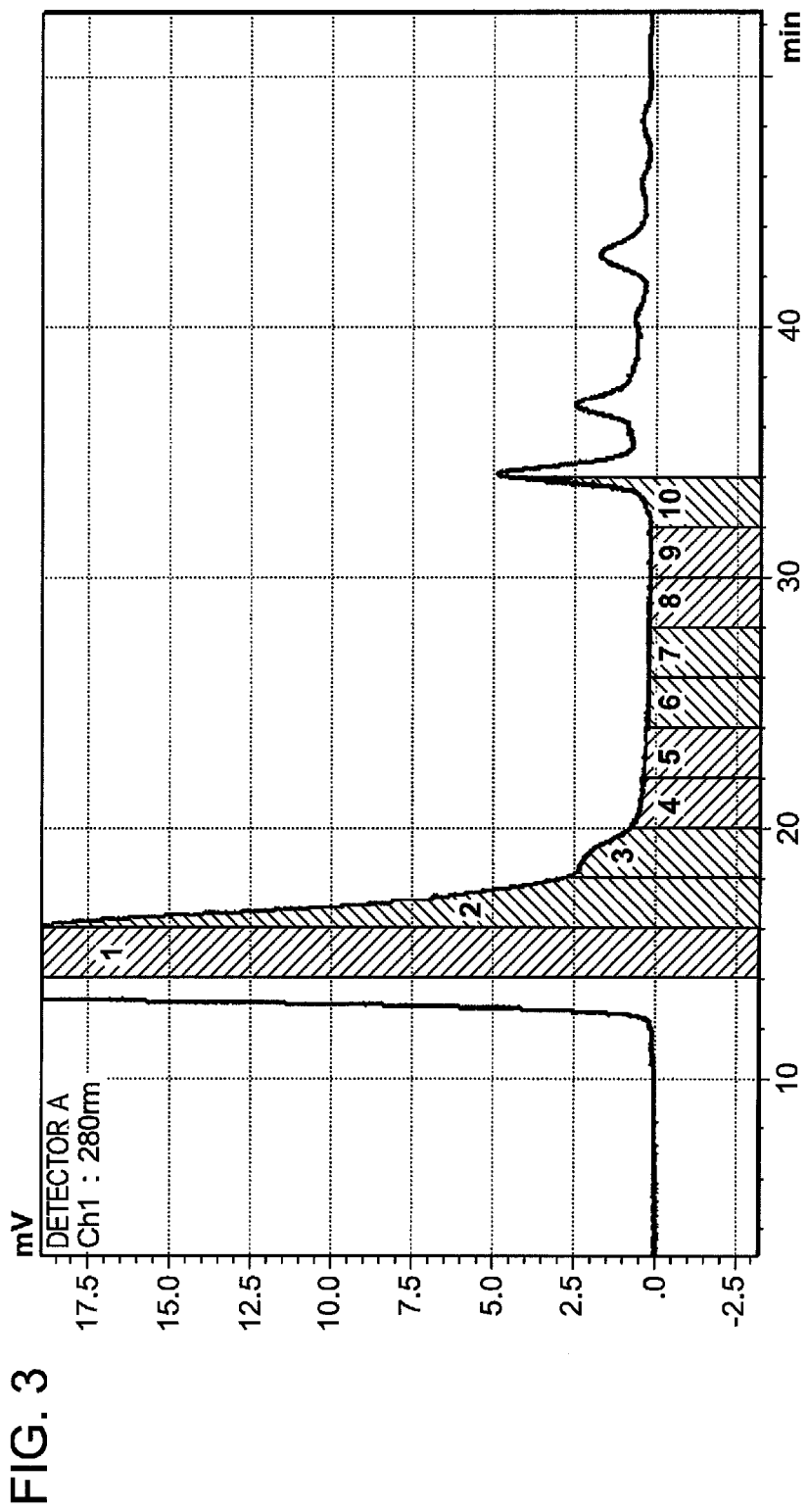
FIG. 3 is an enlarged view of part of a spectrum shown in FIG. 2.
Figure 4:
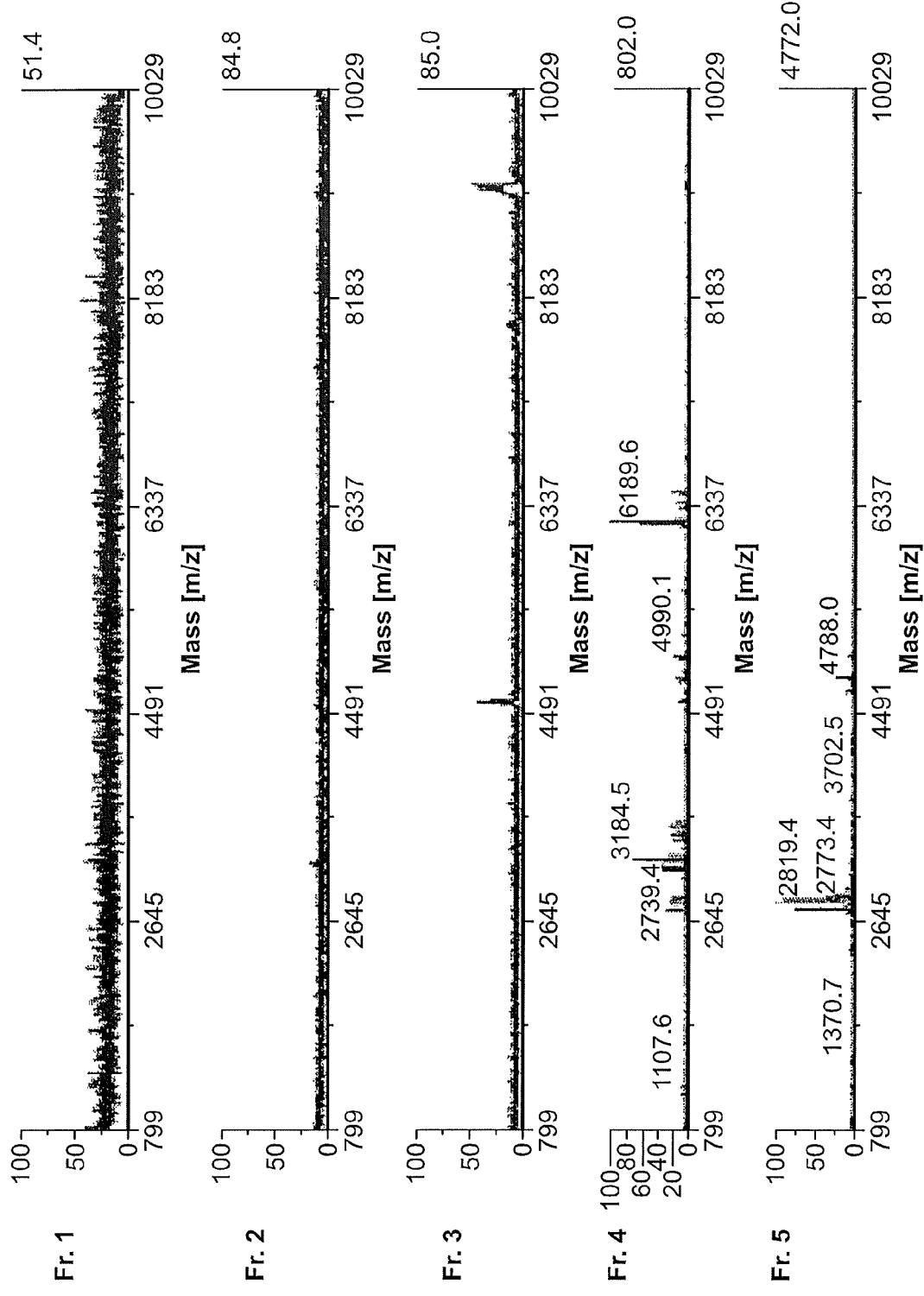
FIG. 4 shows MS spectra of the fractionated serum sample, demonstrating the effective separation and enrichment of serum peptidome subfractions (1,000<molecular weight<5,000).
Figure 4:
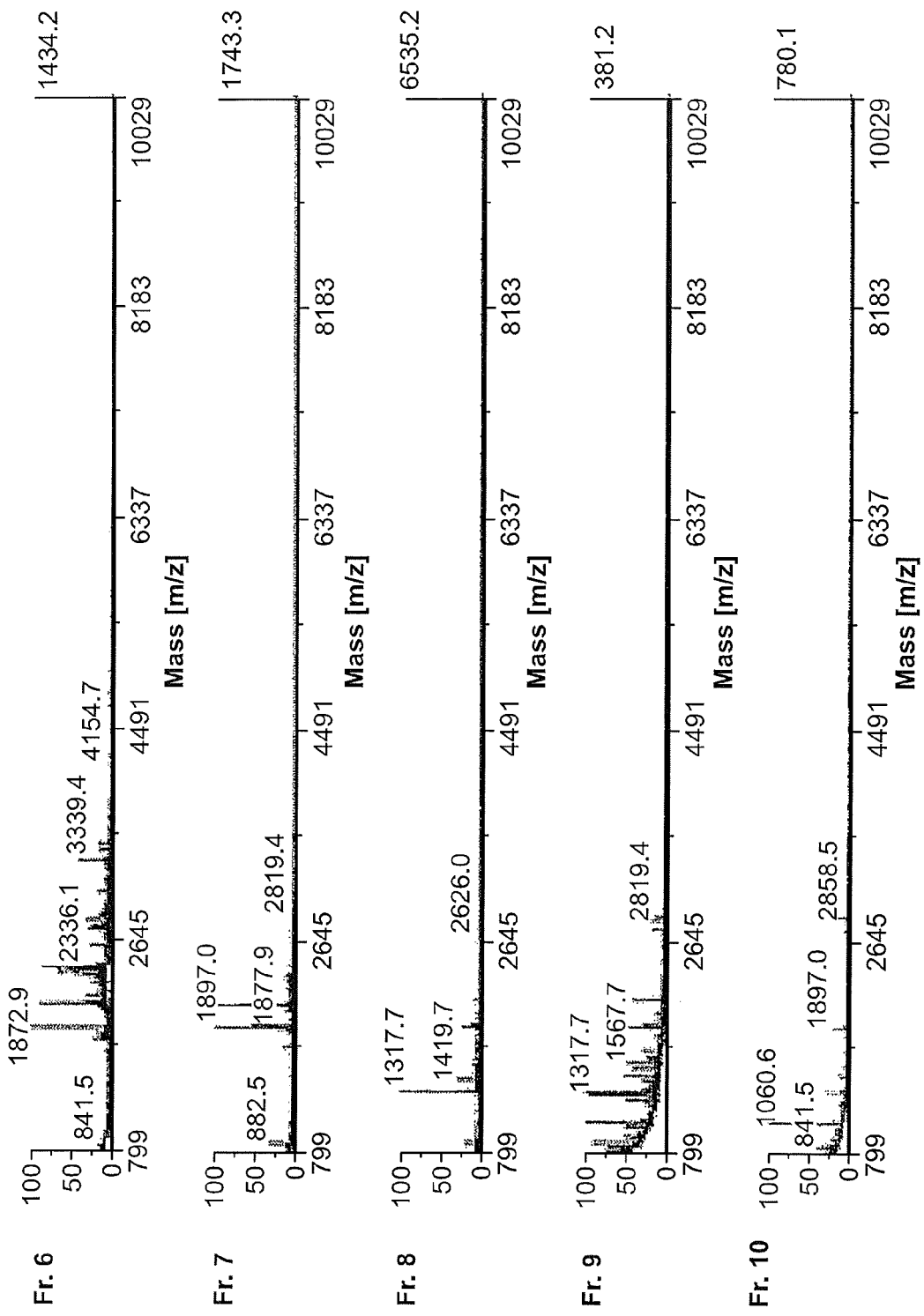

Next, the accuracy of size exclusion chromatography was assessed with a MALDI-TOF-TOF mass spectrometer. FIG. 3 is an enlarged view of part of one spectrum of the gel filtration HPLC. The accuracy of size exclusion chromatography was assessed by analyzing ten fractions (2 min each from retention time 14 min. to 34 min.) indicated by shaded regions "1" to "10" in FIG. 3 with the MALDI-TOF-TOF mass spectrometer. The results are shown in FIG. 4. FIG. 4 shows the respective MS spectra of the 10 fractions (Fr. 1 to Fr. 10). As shown by the continuous MS spectra in FIG. 4, the gel filtration chromatography procedure allowed precise separation of serum proteins and peptides according to molecular weights.

Based on the results shown in FIG. 4, the six fractions (from retention time 22 min. to 34 min.) indicated by the shaded regions "5" to "10" in FIG. 3 were defined and collected as peptidome fractions. These fractions correspond to molecular weights of 1,000 to 5,000.

The collected fractions (peptide samples) were dried-up with a Vacuum Spin Drier (TAITEC).

Example 3

Peptide Biomarker Screening

For exploration of serum peptides which had a potential to be used for the early detection of lung cancer, quantitative peptidome profiles of serum samples were acquired from 92 individuals including normal healthy persons and lung cancer patients. Table 3 shows a breakdown of the 92 individuals.

TABLE 3

| Group | Case number (Male/Female) | Averaged age |
|---|---|---|
| Healthy controls | 30 (20/10) | 56.7 |
| Lung adenocarcinoma stage-I | 10 (7/3) | 63.7 |
| Lung adenocarcinoma stage-II | 10 (6/4) | 63.1 |
| Lung adenocarcinoma stage-IIIa | 12 (8/4) | 63.6 |
| Lung adenocarcinoma stage-IIIb | 15 (10/5) | 64.0 |
| Lung adenocarcinoma stage-IV | 15 (10/5) | 63.7 |

Out of the 92 individuals, 62 individuals were lung cancer patients. Out of the 62 lung cancer patients, 32 individuals were operable stage lung cancer patients (stage-I: n=10, stage-II: n=10, stage-IIIa: n=12) and the remaining 30 individuals were advanced stage lung cancer patients (stage-IIIb: n=15, stage-IV: n=15). This made it possible to acquire biomarkers reflecting lung cancer progression.

First, sera were collected in the same manner as in Example 1. Further, the serum samples were purified with gel filtration chromatography in the same manner as in Example 2. The resulting 92 peptide samples were individually subjected to LC/MS/MS analysis. Specifically, the resulting peptide samples (dried peptidome fractions) were resuspended in 2% acetonitrile with 0.1% trifluoroacetic acid. These peptide samples were analyzed by a QSTAR-Elite mass spectrometer (AB Sciex) combined with an UltiMate 3000 nano-flow HPLC system (DIONEX Corporation).

First, the peptide samples were separated on a 100 μm×200 mm tip-column (GL Scientific) in which L-Column beads were manually loaded. The peptide samples were separated using a solvent A (0.1% formic acid, 2% acetonitrile) and a solvent B (0.1% formic acid, 70% acetonitrile) at a flow rate of 200 nl/min. It should be noted here that the solvent B had a multistep liner gradient formed so that the solvent B changed from 5% to 55% for 95 minutes and then changed from 55% to 95% for ten minutes.

The eluate was directly subjected to a 1-second MS survey (m/z 40 to 1800), and the precursor ions (30 counts or more, charge state +2 to +4, m/z range of 50/2000) that were highest in intensity among them were subjected to three MS/MS measurements. It should be noted that the survey conditions were as follows: SIDA=3.0; and maximum accumulation time=2.0 seconds. Previously targeted precursor ions were excluded from repetitive MS/MS acquisition for 40 seconds (with a mass tolerance of 100 mDa).

Figure 5:
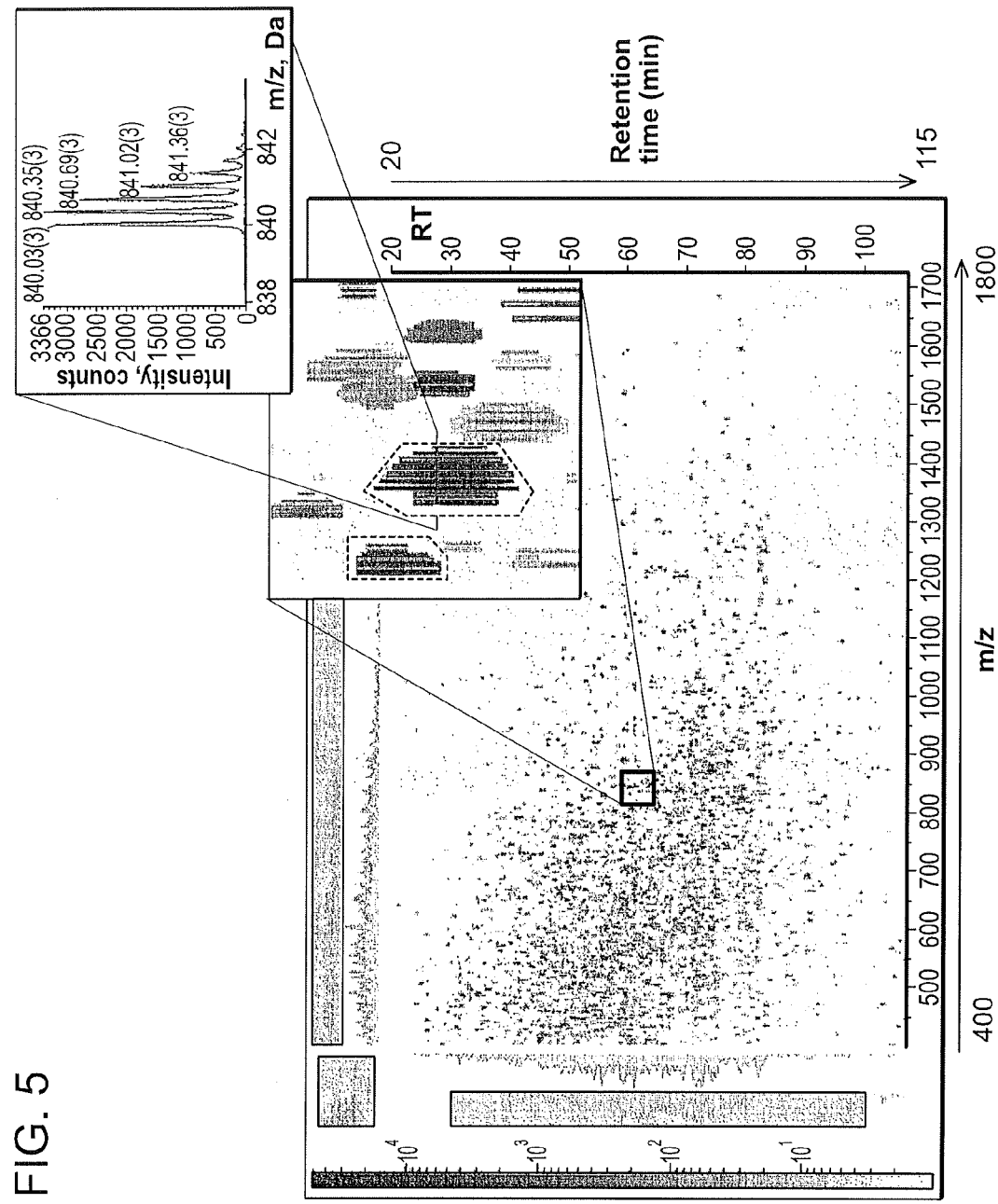
FIG. 5 shows a representative two-dimensional chromatogram plane of mass spectrometry data utilized for the following label-free quantification analysis of multiple samples.

Then, 92 raw data files from QSTAR-Elite (.wiff and .wiff-.scan formatted) were directly loaded onto an Expressionist RefinerMS module (Genedata). This module was used to form MS chromatogram planes as shown in FIG. 5. Further, from all the chromatograms, instrument specific noises and chemical noises were substantially removed by subtraction. Specifically, all the chromatograms were smoothened with RT Window=3 scans in chromatogram chemical noise subtraction activity. For removal of the background noises, a peak intensity was defined as follows:

$$Intensity_{subtracted} = \max(Intensity_{original} - Quantile-Threshold, 0),$$

where max is a function that takes a large argument from among arguments, Quantile takes on a value of 50%, and Intensity Threshold takes on a value of 15 cps. Furthermore, signals satisfying at least one of the following criteria were considered as noise peaks and removed by subtraction:

RT Window>50 scans
Minimum RT Length=4 scans
Minimum m/z length=8 data points.

Figure 6:
FIG. 6 shows a representative result of the retention time alignment of 92 two-dimensional chromatogram planes.
Figure 6:
Figure 6:
Figure 6:
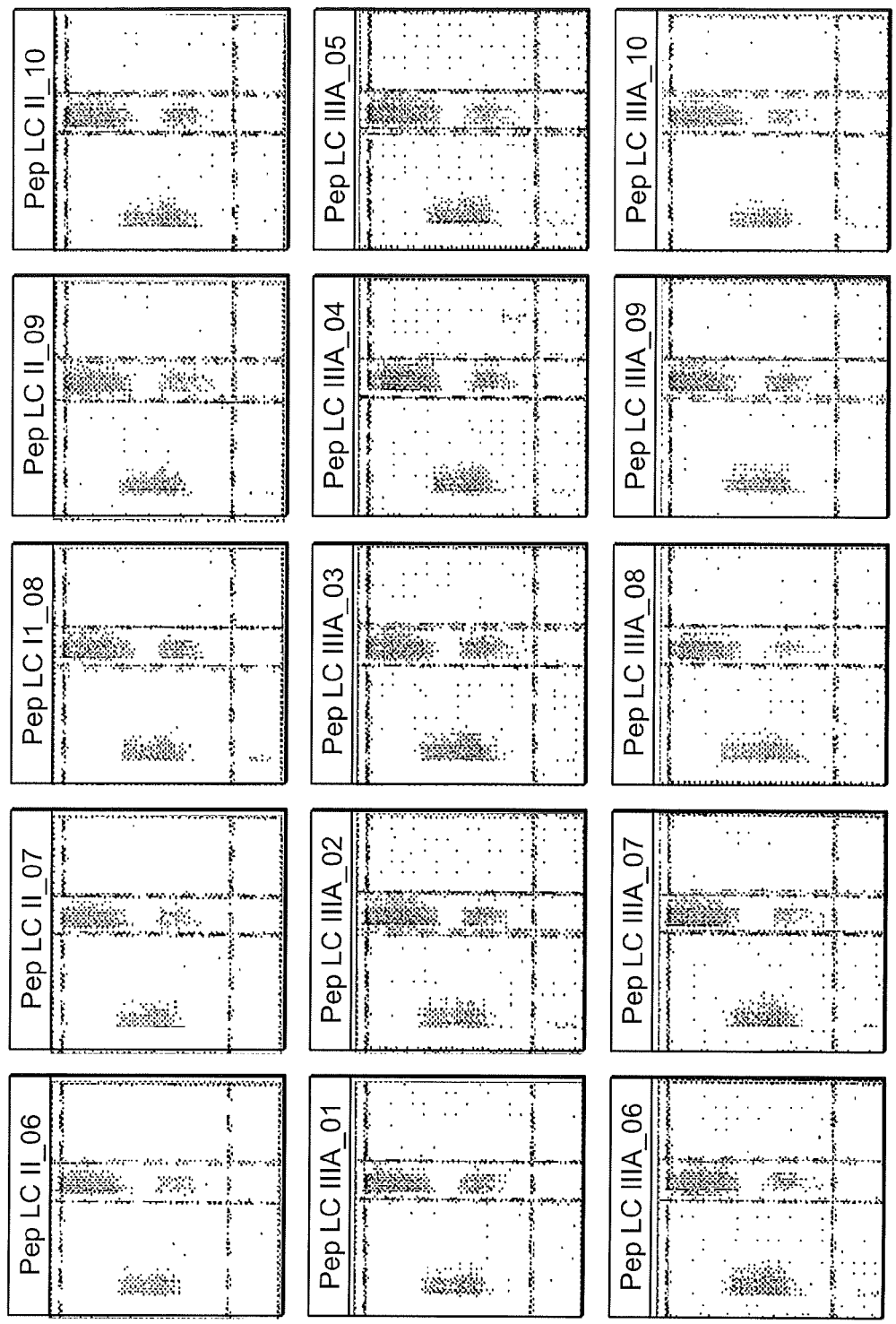
Figure 6:
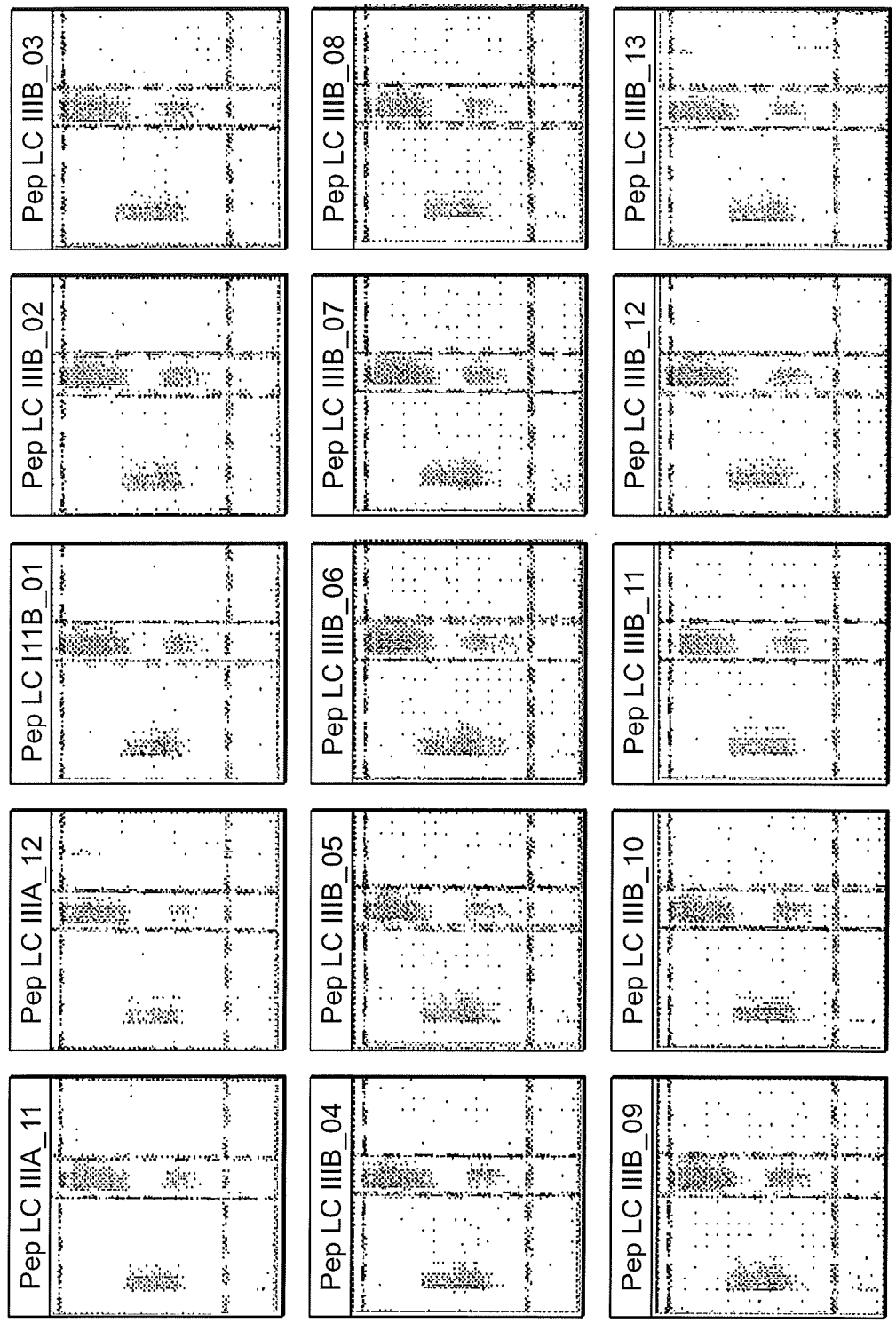
Figure 6:

Then, the retention time grids on each MS chromatogram plane were perfectly aligned among 92 chromatogram planes. Some of the results of the alignment are shown in FIG. 6. The alignment allows solid quantification analysis using multiple samples. The parameters in chromatogram RT alignment activity in the alignment are as follows:

m/z Window=0.1 Da
RT Window=0.2 min
Gap Penalty=1
RT search interval=5 min.

Next, peaks were detected from temporarily averaged chromatograms by chromatogram summed peak detection activity in order to surely acquire location information of peaks not detectable in particular planes. The parameters were as follows:

Summation Window=5 scans
Overlap=50
Minimum Peak Size=4 scan
Maximum Merge Distance=10 data points
Gap/Peak Ratio=1
Method=curvature-based peak detection
Peak Refinement Threshold=5
Consistency Filter Threshold=0.8
Signal/Noise Threshold=1.

After that, isotope patterns were identified from among 2D peaks by two-step summed isotope clustering activity. Isotopic peaks belonging to the same peptide signals were grouped as peak clusters. Some examples of the clusters are indicated by dashed frames in FIG. 5. The first clustering was performed with the following criteria:

Minimum Charge=1
Maximum Charge=10
Maximum Missing Peaks=0
First Allowed Gap Position=3
Ionization=protonation
RT Tolerance=0.1 min
m/z Tolerance=0.05 Da
Isotope Shape Tolerance=10.0
Minimum Cluster Size Ratio=1.2.

The second clustering was performed in the same settings as the first clustering except for the following criteria:

Minimum Cluster Size Ratio=0.6
Reuse Existing Clusters=true.

In the result, 12,396 non-redundant peak clusters with charge state +1 to +10 were detected from the 92 serum samples.

Information on all detected cluster peaks (including m/z, retention time, and intensity) was exported as ABS files.

The ABS files thus exported were loaded on an Expressionist Analyst module. From among the peak clusters, 3,537 peak clusters with charge state +2 to +6 were utilized for further consideration.

Student's t-test was performed between the group of normal healthy persons (n=30) and the group of lung cancer patients (n=62) in order to extract peptides showing lung cancer-specific changes in their serum levels. Variations in peak intensity among the 92 serum samples in Student's t-test were normalized by fixing the median intensity of each serum sample at 10,000. Student's t-test was performed between the group of normal healthy persons and the group of lung cancer patients using the intensity data thus normalized. The result is shown in FIG. 7.

FIG. 7 is a hierarchy chart of clusters (peptides) according Student's t-test p-values. Those peptides whose p-value in the test was p<0.01 and whose difference in intensity between the two groups was five times or greater were extracted as peaks of peptides that can be used as biomarkers. This resulted in the identification of 118 peptides (ID_001 to ID_118 as listed in Table 2).

To assess the statistical efficacy of these 118 peptides for the classification of the 92 subjects into the group of normal healthy persons and the group of lung cancer patients, principal component analysis was performed using these 118 candidate biomarker peptides. The result is shown in FIG. 8. As shown in FIG. 8, the 92 subjects were able to be precisely classified into the group of normal healthy persons and the group of lung cancer patients. That is, the quantitative values of 118 peptides were statistically sufficient to achieve the precise classification between the group of normal healthy persons and the group of lung cancer patients. Therefore, these 118 peptides can be used as biomarkers for detecting lung cancer.

As described above, by the screening of biomarkers using gel filtration chromatography and LC/MS/MS, 118 peptides that can be used as lung cancer biomarkers were obtained.

Example 4

Identification of Peptide Sequences by LC/MS/MS

Comprehensive peptide sequencing was performed using QSTAR-Elite LC/MS/MS and MASCOT database search. The MASCOT database search was performed on Analyst QS 2.0 software (AB Sciex). The MS/MS data was searched against the human protein database from SwissProt 57.4 (20,400 sequences) using the following parameters:
Taxonomy=Homo sapiens
Enzyme=None
Fixed modifications=None
Variable modifications=Oxidation (Met)
MS tolerance=50 ppm
MS/MS tolerance=0.1 Da.
It was recognized that with the expectation value <0.05, a peptide among the MS/MS data consists of a sequence corresponding to the expectation value.

Among 230,657 MS/MS queries from the serum samples of the 92 subjects, 5,382 peptides were sequenced with MASCOT expectation value <0.05. After removing redundancy, 424 types of peptide were identified, corresponding to 106 proteins.

Regarding the 118 peptides, 19 peptides were sequenced, namely 12 peptides derived from fibrinogen alpha chain (FIBA), four peptides from apolipoprotein A-IV (APOA4), one each from amiloride-sensitive cation channel 4 (ACCN4), apolipoprotein E (APOE), and limbin (LBN). The respective amino acid sequences of the 19 peptides are shown above in Table 1.

Example 5

MRM-Based Quantification

To assess the quantitative reproducibility of the peptides as well as the clinical usefulness of the 19 candidate sequenced biomarkers, label-free quantification analysis was performed on additionally-prepared serum samples from 96 subjects, using MRM (multiple reaction monitoring). Table 4 shows a breakdown of the 96 subjects. The subjects in the present example are different from those listed in Table 3.

TABLE 4

| Group | Case number (Male/Female) | Averaged age |
|---|---|---|
| Healthy controls | 36 (26/10) | 63.6 |
| Lung adenocarcinoma stage-I | 10 (7/3) | 64.2 |
| Lung adenocarcinoma stage-II | 10 (7/3) | 62.1 |
| Lung adenocarcinoma stage-IIIa | 11 (7/4) | 66.0 |
| Lung adenocarcinoma stage-IIIb | 15 (10/5) | 64.3 |
| Lung adenocarcinoma stage-IV | 14 (10/4) | 66.4 |

For designing the optimum MRM transitions specific to the 19 peptides, the m/z values of precursor ions detected in the screening phase were set as Q1 channels and those of four most intense fragment ions were selected from each MS/MS spectrum for Q3 channels. Hence totally 76 (19×4) MRM transitions were simultaneously monitored by 4000 QTRAP mass spectrometry using a serum peptidome sample.

As in Example 2, the serum samples collected were processed with Superdex peptide column chromatography before mass spectrometric analyses. The samples (peptides) thus extracted were dried and then resuspended in a tryptic digestion solution containing 2% acetonitrile, 0.1% trifluoroacetic acid, and 1 fmol/µl of BSA. Next, these samples were analyzed by a 4000 QTRAP mass spectrometer (AB Sciex) combined with a Paradigm MS4 PAL nano-flow HPLC system (AMR Inc.).

Figure 9:
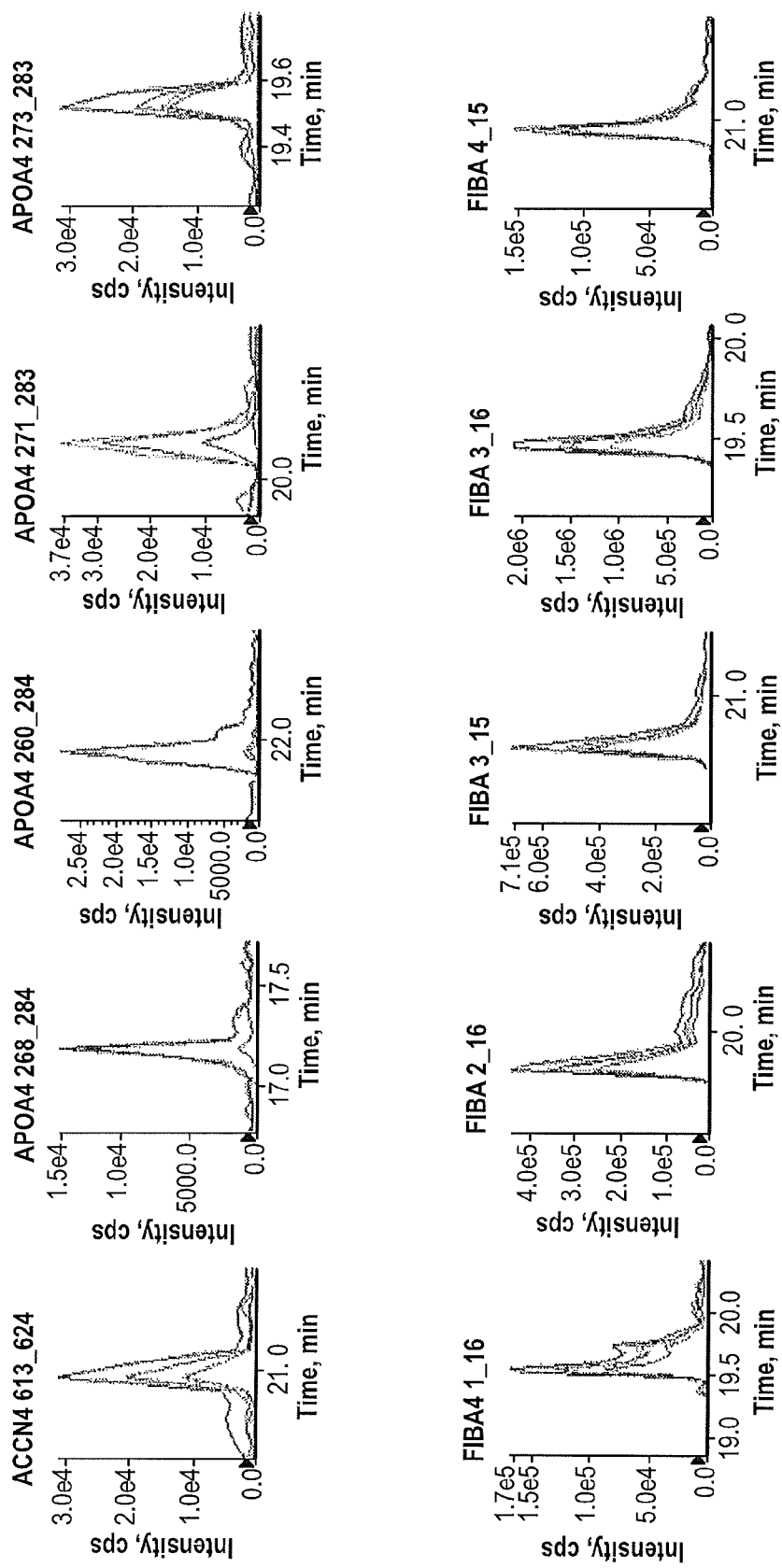
FIG. 9 shows results of simultaneous monitoring of MRM transitions for designating optimum MRM transitions.
Figure 9:
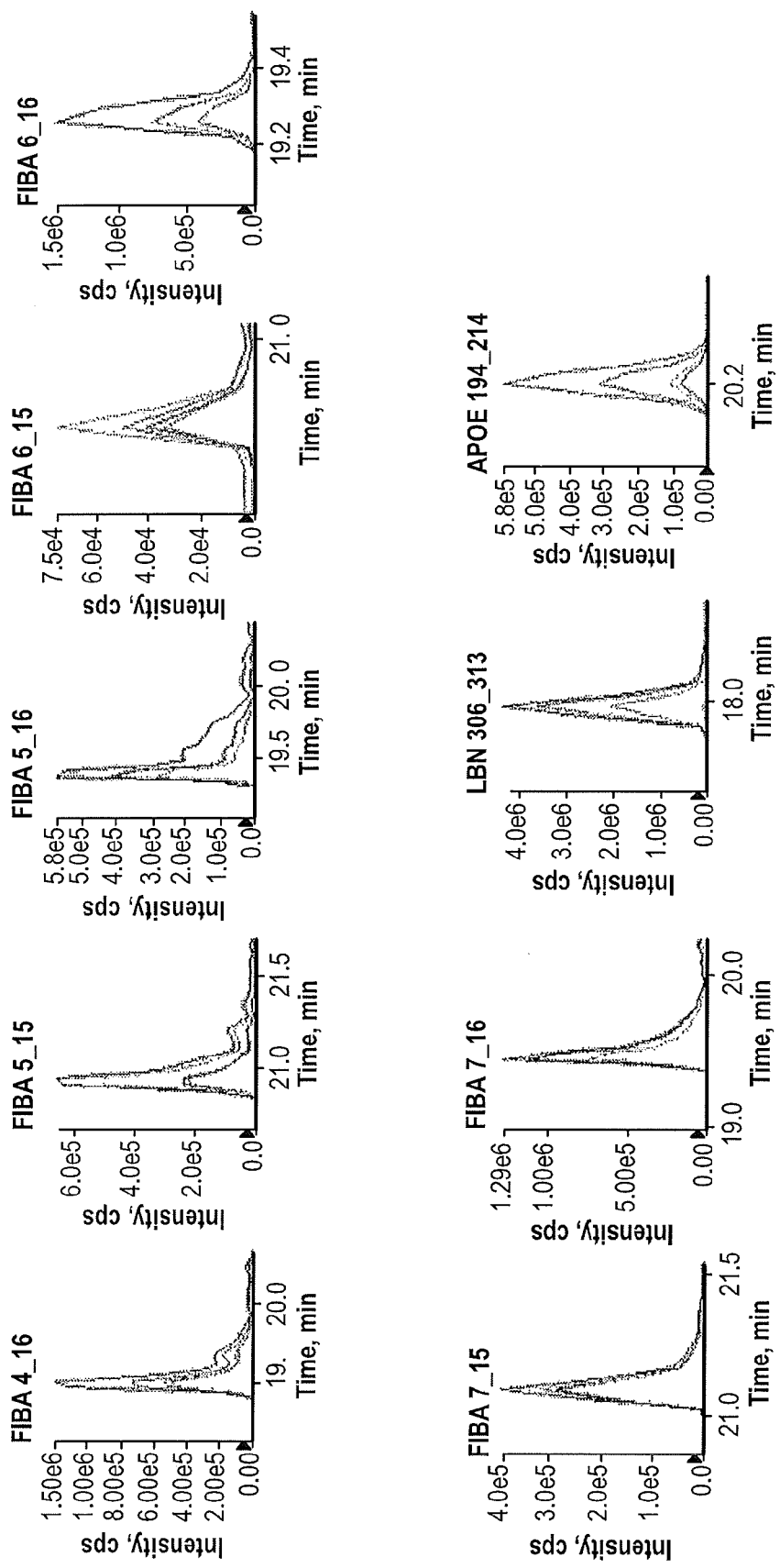

The peptide samples were separated on a 100 µm×100 mm tip-column (GL Scientific) in which L-Column ODS beads (Chemicals Evaluation and Research Institute, Saitama, Japan) were manually loaded. The peptide samples were separated using a solvent A (0.1% formic acid, 2% acetonitrile) and a solvent B (0.1% formic acid, 90% acetonitrile) at a flow rate of 200 nl/min. It should be noted here that the solvent B had a multistep liner gradient formed so that the solvent B changed from 2% to 100% for ten minutes. FIG. 9 shows a result of monitoring of 76 MRM transitions. Each chromatogram in FIG. 9 shows four merged chromatograms obtained by monitoring, with a 4000 QTRAP system, four fragment ions that showed the highest intensity in QSTSR-Elite LC/MS/MS analysis.

The specific eluting retention time was determined for each peptide, and the optimum MRM transitions showing the highest MRM chromatogram peak out of four transitions were selected for each peptide. See Table 5 for information on each of the MRM transitions.

TABLE 5

| Peptide ID | m/z precursor Q1 | m/z fragment (Q3) | Dwell time (msec) | Collision energy |
|---|---|---|---|---|
| ACCN4_613_624 | 551.8 | 175.1 | 25 | 30.3 |
| APOA4_260_284 | 689.8 | 120.1 | 25 | 36.4 |
| APOA4_268_284 | 643.3 | 120.1 | 25 | 34.3 |
| APOA4_271_283 | 750.9 | 259.1 | 25 | 39.0 |
| APOA4_273_283 | 629.8 | 645.3 | 25 | 33.7 |
| APOE_194_214 | 756.4 | 1034.0 | 25 | 25.8 |
| FIBA_1_16 | 768.9 | 645.3 | 25 | 39.8 |
| FIBA_2_16 | 733.3 | 645.3 | 25 | 38.3 |
| FIBA_3_15 | 597.8 | 175.1 | 25 | 32.3 |
| FIBA_3_16 | 675.8 | 645.3 | 25 | 35.7 |
| FIBA_4_15 | 554.3 | 175.1 | 25 | 30.4 |
| FIBA_4_16 | 632.3 | 645.3 | 25 | 33.8 |
| FIBA_5_15 | 525.7 | 175.1 | 25 | 29.1 |
| FIBA_5_16 | 603.8 | 645.3 | 25 | 32.6 |
| FIBA_6_15 | 461.2 | 120.1 | 25 | 26.3 |
| FIBA_6_16 | 539.3 | 645.3 | 25 | 29.7 |
| FIBA_7_15 | 432.7 | 235.1 | 25 | 25.0 |
| FIBA_7_16 | 510.7 | 645.3 | 25 | 28.5 |
| LBN_306_313 | 453.2 | 645.3 | 25 | 25.9 |
| $^a$BSA | 461.8 | 722.4 | 25 | 29.1 |
| $^a$BSA | 464.3 | 651.4 | 25 | 29.3 |
| $^a$BSA | 547.3 | 589.3 | 25 | 32.9 |
| $^a$BSA | 582.3 | 951.5 | 25 | 34.4 |
| $^a$BSA | 653.4 | 1055.6 | 25 | 38 |

$^a$5 fragments of digested BSA were used for data normalization.

Two peptides FIBA 3-16 and FIBA 5-16 showed identical orders of fragment ion intensities between QSTAR-Elite and 4000 QTRAP.

Then, MRM-based relative quantification analysis was performed using serum samples from 36 normal healthy persons (normal controls) and serum samples from 60 lung cancer patients in duplicated experiments.

First, ions of 19 biomarker peptides and ions of 5 BSA-derived peptides were simultaneously monitored by the MRM mode in Analyst 1.5 software (AB Sciex). The acquired MRM chromatogram were then smoothened and quantified with MultiQuant software (AB Sciex). Peak areas in each sample were normalized as follows:

$$\text{Peak Area}_{Normalized} = 1000 \times (\text{Peak Area}_{Raw\ data}) / (\text{summed peak areas of 5 BSA fragments})$$

Figure 10:
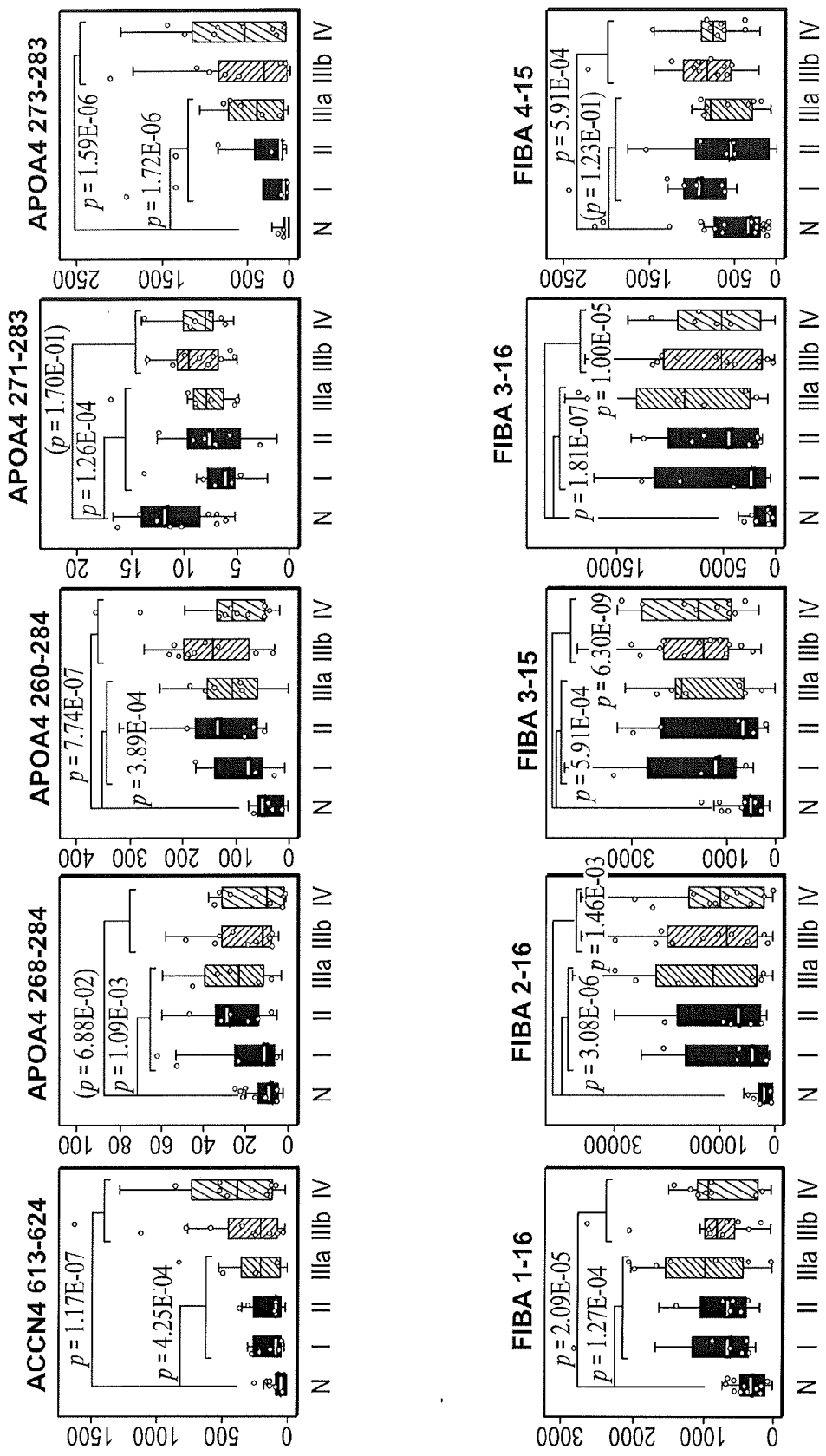
FIG. 10 shows box plots showing results of relative quantification analysis.
Figure 10:
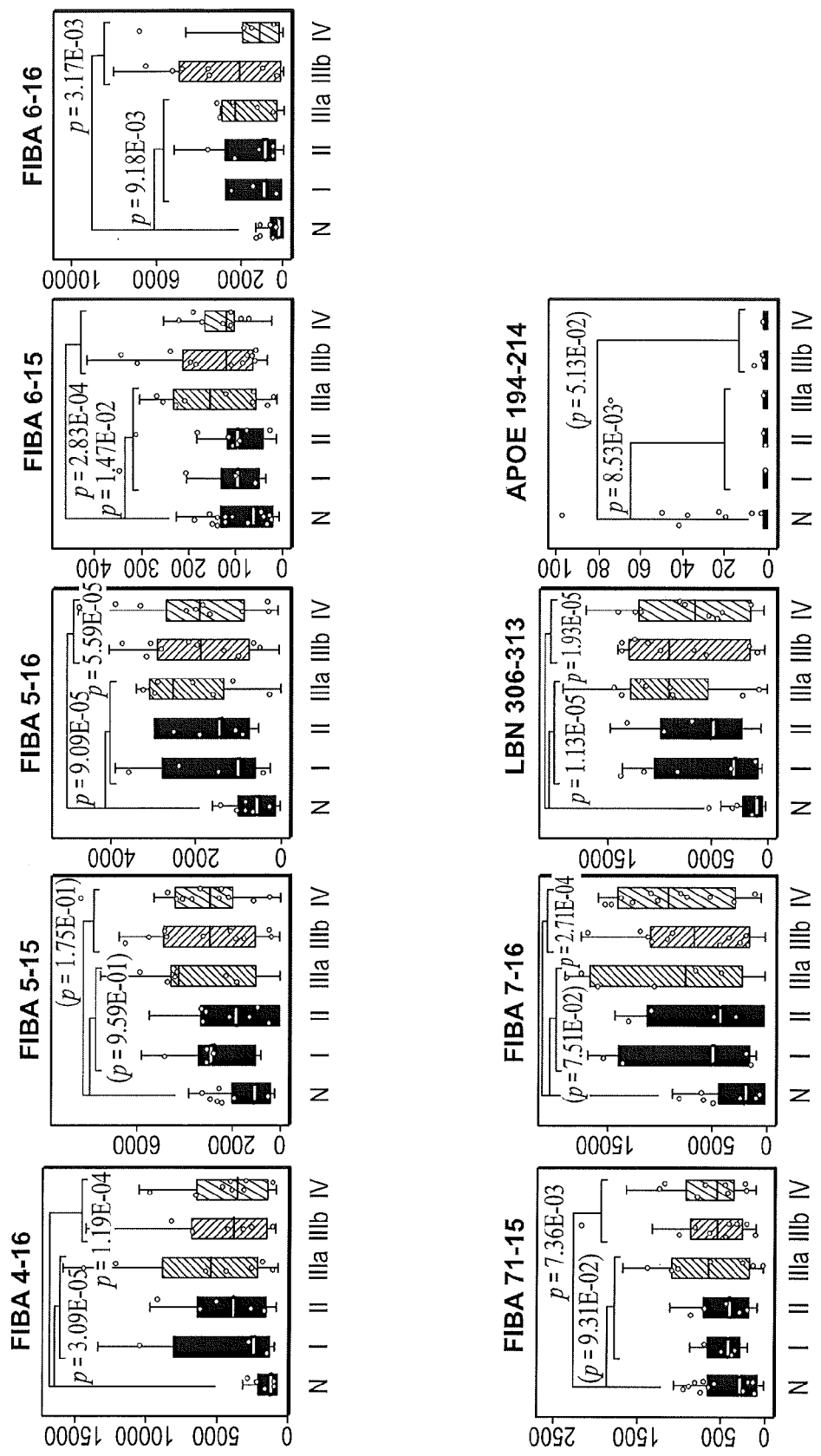

The serum levels of 19 biomarker peptides were calculated from normalized and averaged MRM chromatogram peak areas, and the results of calculation are displayed with box plots in FIG. 10. On the horizontal axis in FIG. 10, "N" represents the serum samples from the normal healthy persons and "I" to "IV" represent the serum samples from the lung cancer stage-I to IV patients, respectively. The box plots were depicted with R algorithm. For each study, the box represents the points stretching from the 25th percentile to the 75th percentile. The line across the box represents the median. The lengths of the lines above and below the box are defined by the maximum and minimum data values, respectively, that lie within 1.5 times the spread of the box.

Example 6

Statistical Evaluation Based on MRM-Based Quantification

To evaluate the efficacy of biomarker peptides for the early detection of lung cancer, the quantification results obtained from the operative stage lung cancer (stage-I, II, and IIIa) group and those obtained from the group of normal healthy persons were compared for evaluation by Student's t-test. The results are shown in FIG. 10.

As shown in FIG. 10, out of the 19 peptides, 15 peptides (ACCN4 613-624, APOA4, 271-283, APOA4 268-284, APOA4 260-284, APOA4 273-283, APOE 194-214, FIBA 1-16, FIBA 2-16, FIBA 5-16, FIBA 6-15, FIBA 6-16, FIBA 4-16, FIBA 3-15, FIBA 3-16, LBN 306-313) showed significant differences in their serum levels between the two groups ($p<0.05$). On the other hand, the remaining 4 peptides (FIBA 4-15, FIBA 5-15, FIBA 7-15, and FIBA 7-16) did not show significant differences ($p<0.05$).

Similarly, the advanced stage lung cancer (stage-IIIb and IV) was compared with the group of normal healthy persons by Student's t-test for the 19 polypeptides. The results are shown in FIG. 10.

As shown in FIG. 10, 15 peptides (ACCN4 613-624, APOA4 260-284, APOA4 273-283, FIBA 1-16, FIBA 7-15, FIBA 7-16, FIBA 2-16, FIBA 5-16, FIBA 6-15, FIBA 6-16, FIBA 4-15, FIBA 4-16, FIBA 3-15, FIBA 3-16, LBN 306-313) showed significant differences in their serum levels between the two groups ($p<0.05$). On the other hand, the remaining four peptides (APOA4 268-284, APOA4 271-283, FIBA 5-15, and APOE 194-214) did not show significant differences ($p<0.05$).

Furthermore, the sensitivity and specificity of the biomarkers were assessed by ROC curve analysis. The ROC curves were depicted by the R algorithm. The cut-off values was set at the point whose distance from the (sensitivity, specificity)= (1, 1) reached the minimum. Part of the analysis result is shown in FIG. 11. In FIG. 11, "Sens", "Spec", "PV+", and "PV−" represent the sensitivity, the specificity, the positive predictive value, and the negative predictive value, respectively.

Given the values of sensitivity to detect operable stage lung cancer patients, FIBA 6-15 (87.1%), APOA4 273-283 (61.3%), FIBA 5-16 (58.1%), and LBN 306-313 (58.1%) were shown to be superior biomarkers. Among them, APOA4 273-283, FIBA 5-16, and LBN 306-313 were remarkably higher in specificity (88.9%, 94.4%, and 100%, respectively). Hence these three peptides were shown to be more effective biomarkers for the early detection of lung cancer.

INDUSTRIAL APPLICABILITY

As described above, the present invention can detect early-stage lung cancer. Therefore, the present invention can be widely used in the field of diagnostic medicine and the field of healthcare.

Sequence Listing

The invention claimed is:

1. A method for diagnosing or aiding in diagnosing lung cancer in a living organism, comprising the steps of:

measuring, in a sample collected from the living organism, at least one lung cancer diagnostic polypeptide consisting of the amino acid sequence of SEQ ID NO: 19; and comparing the level of the at least one lung cancer diagnostic polypeptide in the sample to a control value, wherein an increase in the level in the sample relative to the control is indicative of lung cancer.

2. The method as set forth in claim 1, further comprising the step of obtaining a lung cancer diagnostic polypeptide fraction by subjecting the sample to gel filtration chromatography and measuring, in the fraction thus obtained, the at least one lung cancer diagnostic polypeptide.

3. The method as set forth in claim 1, wherein the sample is blood, serum, or plasma.

4. The method as set forth in claim 1, wherein the sample is subjected to heat treatment prior to the measurement step.

5. The method as set forth in claim 1, further comprising measuring and comparing one or more lung cancer diagnostic polypeptides of SEQ ID NO: 5 and/or 12.

6. The method as set forth in claim 1, further comprising measuring and comparing the lung cancer diagnostic polypeptides of SEQ ID NO: 5 and 12.

7. The method as set forth in claim 1, further comprising measuring one or more lung cancer diagnostic polypeptides selected from SEQ ID NOS: 1 to 18.

8. The method as set forth in claim 1, wherein the lung cancer is adenocarcinoma, squamous cell carcinoma, or large cell carcinoma.

9. The method as set forth in claim 1, wherein the lung cancer is adenocarcinoma.

10. The method as set forth in claim 1, wherein the lung cancer is early-stage lung cancer.

11. The method as set forth in claim 1, further comprising determining a stage of the lung cancer.

12. The method as set forth in claim 11, wherein the lung cancer is early-stage lung cancer.

13. A method for diagnosing or aiding in diagnosing lung cancer in a living organism, comprising the steps of:

collecting a sample from the living organism;
using mass spectrometry to measure, in the sample, the level at least one lung cancer diagnostic polypeptide consisting of the amino acid sequence of SEQ ID NO: 19; and
comparing the level of the at least one lung cancer diagnostic polypeptide in the sample to a control value, wherein an increase in the level in the sample relative to the control is indicative of lung cancer.

14. The method of claim 13, wherein the measuring uses a tandem mass spectrometer (MS/MS).

15. The method as set forth in claim 13, further comprising measuring and comparing the lung cancer diagnostic polypeptides of SEQ ID NO: 5 and/or 12.

16. The method of claim 13, further comprising measuring and comparing the lung cancer diagnostic polypeptides of SEQ ID NO: 5 and 12.

17. The method as set forth in claim 13, further comprising measuring and comparing one or more lung cancer diagnostic polypeptides of SEQ ID NOS: 1 to 18.

18. The method of claim 13, wherein the lung cancer is adenocarcinoma, squamous cell carcinoma, or large cell carcinoma.

19. The method of claim 13, wherein the lung cancer is adenocarcinoma.

20. The method of claim 13, further comprising determining a stage of the lung cancer.

21. The method of claim 13, wherein the lung cancer is early-stage lung cancer.

* * * * *

SEQUENCE LISTING

```
<160> NUMBER OF SEQ ID NOS: 19

<210> SEQ ID NO 1
<211> LENGTH: 12
<212> TYPE: PRT
```

<213> ORGANISM: Homo sapiens

<400> SEQUENCE: 1

Cys Pro Ser Leu Gly Arg Ala Glu Gly Gly Val
1               5                   10

<210> SEQ ID NO 2
<211> LENGTH: 13
<212> TYPE: PRT
<213> ORGANISM: Homo sapiens

<400> SEQUENCE: 2

Glu Leu Gly Gly His Leu Asp Gln Gln Val Glu Glu Phe
1               5                   10

<210> SEQ ID NO 3
<211> LENGTH: 17
<212> TYPE: PRT
<213> ORGANISM: Homo sapiens

<400> SEQUENCE: 3

Ser Leu Ala Glu Leu Gly Gly His Leu Asp Gln Gln Val Glu Glu Phe
1               5                   10                  15

Arg

<210> SEQ ID NO 4
<211> LENGTH: 25
<212> TYPE: PRT
<213> ORGANISM: Homo sapiens

<400> SEQUENCE: 4

Gly Asn Thr Glu Gly Leu Gln Lys Ser Leu Ala Glu Leu Gly Gly His
1               5                   10                  15

Leu Asp Gln Gln Val Glu Glu Phe Arg
            20                  25

<210> SEQ ID NO 5
<211> LENGTH: 11
<212> TYPE: PRT
<213> ORGANISM: Homo sapiens

<400> SEQUENCE: 5

Gly Gly His Leu Asp Gln Gln Val Glu Glu Phe
1               5                   10

<210> SEQ ID NO 6
<211> LENGTH: 21
<212> TYPE: PRT
<213> ORGANISM: Homo sapiens

<400> SEQUENCE: 6

Thr Val Gly Ser Leu Ala Gly Gln Pro Leu Gln Glu Arg Ala Gln Ala
1               5                   10                  15

Trp Gly Glu Arg Leu
            20

<210> SEQ ID NO 7
<211> LENGTH: 16
<212> TYPE: PRT
<213> ORGANISM: Homo sapiens

<400> SEQUENCE: 7

Ala Asp Ser Gly Glu Gly Asp Phe Leu Ala Glu Gly Gly Gly Val Arg
1               5                   10                  15

```
<210> SEQ ID NO 8
<211> LENGTH: 9
<212> TYPE: PRT
<213> ORGANISM: Homo sapiens

<400> SEQUENCE: 8

Asp Phe Leu Ala Glu Gly Gly Gly Val
1               5

<210> SEQ ID NO 9
<211> LENGTH: 10
<212> TYPE: PRT
<213> ORGANISM: Homo sapiens

<400> SEQUENCE: 9

Asp Phe Leu Ala Glu Gly Gly Gly Val Arg
1               5                   10

<210> SEQ ID NO 10
<211> LENGTH: 15
<212> TYPE: PRT
<213> ORGANISM: Homo sapiens

<400> SEQUENCE: 10

Asp Ser Gly Glu Gly Asp Phe Leu Ala Glu Gly Gly Gly Val Arg
1               5                   10                  15

<210> SEQ ID NO 11
<211> LENGTH: 11
<212> TYPE: PRT
<213> ORGANISM: Homo sapiens

<400> SEQUENCE: 11

Glu Gly Asp Phe Leu Ala Glu Gly Gly Gly Val
1               5                   10

<210> SEQ ID NO 12
<211> LENGTH: 12
<212> TYPE: PRT
<213> ORGANISM: Homo sapiens

<400> SEQUENCE: 12

Glu Gly Asp Phe Leu Ala Glu Gly Gly Gly Val Arg
1               5                   10

<210> SEQ ID NO 13
<211> LENGTH: 10
<212> TYPE: PRT
<213> ORGANISM: Homo sapiens

<400> SEQUENCE: 13

Gly Asp Phe Leu Ala Glu Gly Gly Gly Val
1               5                   10

<210> SEQ ID NO 14
<211> LENGTH: 11
<212> TYPE: PRT
<213> ORGANISM: Homo sapiens

<400> SEQUENCE: 14

Gly Asp Phe Leu Ala Glu Gly Gly Gly Val Arg
1               5                   10

<210> SEQ ID NO 15
```

```
<211> LENGTH: 12
<212> TYPE: PRT
<213> ORGANISM: Homo sapiens

<400> SEQUENCE: 15

Gly Glu Gly Asp Phe Leu Ala Glu Gly Gly Gly Val
1               5                   10

<210> SEQ ID NO 16
<211> LENGTH: 13
<212> TYPE: PRT
<213> ORGANISM: Homo sapiens

<400> SEQUENCE: 16

Gly Glu Gly Asp Phe Leu Ala Glu Gly Gly Gly Val Arg
1               5                   10

<210> SEQ ID NO 17
<211> LENGTH: 13
<212> TYPE: PRT
<213> ORGANISM: Homo sapiens

<400> SEQUENCE: 17

Ser Gly Glu Gly Asp Phe Leu Ala Glu Gly Gly Gly Val
1               5                   10

<210> SEQ ID NO 18
<211> LENGTH: 14
<212> TYPE: PRT
<213> ORGANISM: Homo sapiens

<400> SEQUENCE: 18

Ser Gly Glu Gly Asp Phe Leu Ala Glu Gly Gly Gly Val Arg
1               5                   10

<210> SEQ ID NO 19
<211> LENGTH: 8
<212> TYPE: PRT
<213> ORGANISM: Homo sapiens

<400> SEQUENCE: 19

Phe Leu Leu Ser Leu Val Leu Thr
1               5
```